(12) United States Patent
Edwards et al.

(10) Patent No.: US 8,628,754 B2
(45) Date of Patent: *Jan. 14, 2014

(54) HIGHLY EFFICIENT DELIVERY OF A LARGE THERAPEUTIC MASS AEROSOL

(75) Inventors: David A. Edwards, Cambridge, MA (US); Richard P. Batycky, Newton, MA (US); Lloyd Johnston, Newton, MA (US)

(73) Assignee: Civitas Therapeutics, Inc., Chelsea, MA (US)

( * ) Notice: Subject to any disclaimer, the term of this patent is extended or adjusted under 35 U.S.C. 154(b) by 14 days.

This patent is subject to a terminal disclaimer.

(21) Appl. No.: 13/334,236

(22) Filed: Dec. 22, 2011

(65) Prior Publication Data

US 2012/0093893 A1 Apr. 19, 2012

Related U.S. Application Data

(63) Continuation of application No. 12/253,449, filed on Oct. 17, 2008, now abandoned, which is a continuation of application No. 09/878,146, filed on Jun. 8, 2001, now Pat. No. 7,556,798, and a continuation-in-part of application No. 09/591,307, filed on Jun. 9, 2000, now Pat. No. 6,858,199.

(51) Int. Cl.
*A61K 9/14* (2006.01)

(52) U.S. Cl.
USPC ............................ 424/46; 424/489; 424/499

(58) Field of Classification Search
USPC ........................................... 424/46, 489, 499
See application file for complete search history.

(56) References Cited

U.S. PATENT DOCUMENTS

| | | | | |
|---|---|---|---|---|
| 6,518,239 B1 * | 2/2003 | Kuo et al. | ..................... | 514/21.9 |
| 6,565,885 B1 * | 5/2003 | Tarara et al. | ................... | 424/489 |
| 6,858,199 B1 * | 2/2005 | Edwards et al. | ................ | 424/45 |
| 6,921,528 B2 * | 7/2005 | Edwards et al. | ................ | 424/45 |
| 7,556,798 B2 * | 7/2009 | Edwards et al. | ................ | 424/45 |

FOREIGN PATENT DOCUMENTS

WO WO 9744013 * 11/1997

OTHER PUBLICATIONS

Cipola et al, Respiratory Drug Delivery VII 2000. Bolus administration of INS365: studying the feasability of delivering high dose drugs using the AERx pulmonary delivery sysytem.*

* cited by examiner

*Primary Examiner* — Mina Haghighatian
(74) *Attorney, Agent, or Firm* — Darlene A. Vanstone, Esq.; Carolyn S. Elmore, Esq.; Elmore Patent Law Group, P.C.

(57) ABSTRACT

A method for delivering an agent to the pulmonary system, in a single, breath-activated step or a single breath, comprises administering from a receptacle enclosing a mass of particles, to a subject's respiratory tract, particles which have a tap density of less than 0.4 g/cm$^3$ and deliver at least about 50% of the mass of particles. The particles are capable of carrying agents. The agent is (1) part of the spray-drying pre-mixture and thereby incorporated into the particles, (2) added to separately-prepared particles so that the agent is in chemical association with the particles or (3) blended so that the agent is mixed with, and co-delivered with the particles.

Figure 1:
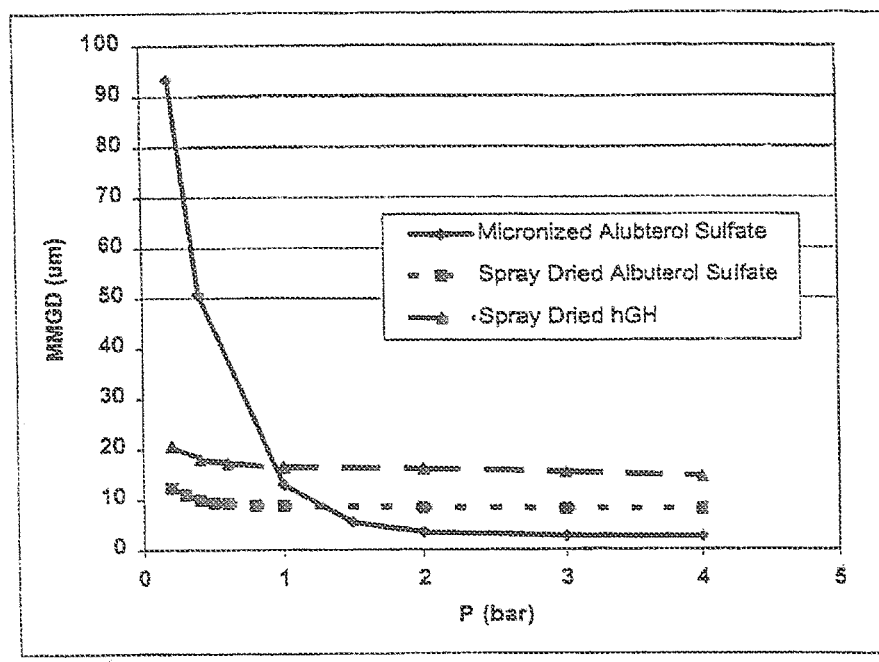

Respirable compositions comprising carrier particles having a tap density of less than 0.4 g/cm$^3$ and a composition comprising an agent are also disclosed. Methods of delivering these respirable compositions are also included.

8 Claims, 21 Drawing Sheets

FIG. 2A

FIG. 2B

HIGHLY EFFICIENT DELIVERY OF A LARGE THERAPEUTIC MASS AEROSOL

RELATED APPLICATION

This application is a continuation of U.S. application Ser. No. 12/253,449, filed Oct. 17, 2008, which is a continuation of U.S. application Ser. No. 09/878,146, filed Jun. 8, 2001, now U.S. Pat. No. 7,556,798, issued Jul. 7, 2009, which is a continuation-in-part of U.S. application Ser. No. 09/591,307, filed Jun. 9, 2000, now U.S. Pat. No. 6,858,199, issued Feb. 22, 2005. This application also claims priority to U.S. application Ser. No. 09/337,245, filed Jun. 22, 1999, now abandoned. The contents of these applications incorporated herein by reference in their entirety.

BACKGROUND OF THE INVENTION

Aerosols for the delivery of therapeutic agents to the respiratory tract have been described, for example, Adjei, A. and Garren, J. Pharm. Res., 7:565-569 (1990); and Zanen, P. and Lamm, J.-W. J., Int. J. Pharm., 114:111-115 (1995). The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchioli which then lead to the ultimate respiratory zone, the alveoli, or deep lung. Gonda, I., "Aerosols for delivery of therapeutic and diagnostic agents to the respiratory tract," in *Critical Reviews in Therapeutic Drug Carrier Systems*, 6:273-313 (1990). The deep lung or alveoli are the primary target of inhaled therapeutic aerosols for systemic drug delivery.

Inhaled aerosols have been used for the treatment of local lung disorders including asthma and cystic fibrosis (Anderson, Am. Rev. Respir. Dis., 140:1317-1324 (1989)) and have potential for the systemic delivery of peptides and proteins as well (Patton and Platz, Advanced Drug Delivery Reviews, 8:179-196 (1992)).

Relatively high bioavailability of many molecules, including macromolecules, can be achieved via inhalation. Wall, D. A., Drug Delivery, 2:1-20 (1995); Patton, J. and Platz, R., Adv. Drug Del. Rev., 8:179-196 (1992); and Byron, P., Adv. Drug. Del. Rev., 5:107-132 (1990). As a result, several aerosol formulations of therapeutic drugs are in use or are being tested for delivery to the lung. Patton, J. S., et al., J. Controlled Release, 28:79-85 (1994); Damms, B. and Bains, W., Nature Biotechnology (1996); Niven, R. W. et al., Pharm. Res., 12(9): 1343-1349 (1995); and Kobayashi, S. et al., Pharm. Res., 13(1):80-83 (1996).

However, pulmonary drug delivery strategies present many difficulties, in particular, for the delivery of macromolecules; these include protein denaturation during aerosolization, excessive loss of inhaled drug in the oropharyngeal cavity (often exceeding 80%), poor control over the site of deposition, lack of reproducibility of therapeutic results owing to variations in breathing patterns, the frequent too-rapid absorption of drug potentially resulting in local toxic effects, and phagocytosis by lung macrophages.

In addition, many of the devices currently available for inhalation therapy are associated with drug losses. Considerable attention has been devoted to the design of therapeutic aerosol inhalers to improve the efficiency of inhalation therapies. Timsina et al., Int. J. Pharm., 101:1-13 (1995) and Tansey, I. P., Spray Technol. Market, 4:26-29 (1994). Attention has also been given to the design of dry powder aerosol surface texture, regarding particularly the need to avoid particle aggregation, a phenomenon which considerably diminishes the efficiency of inhalation therapies. French, D. L., Edwards, D. A. and Niven, R. W., J. Aerosol Sci., 27:769-783 (1996).

Dry powder formulations (DPF's) are gaining increased interest as aerosol formulations for pulmonary delivery. Damms, B. and W. Bains, Nature Biotechnology, (1996); Kobayashi, S., et al., Pharm. Res., 13(1):80-83 (1996); and Timsina, M. et al., Int. J. Pharm., 101:1-13 (1994). Dry powder aerosols for inhalation therapy are generally produced with mean geometric diameters primarily in the range of less than 5 μm. Ganderton, D., J. Biopharmaceutical Sciences, 3:101-105 (1992) and Gonda, I., "Physico-Chemical Principles in Aerosol Delivery," *Topics in Pharmaceutical Sciences* (1991), Crommelin, D. J. and K. K. Midha, Eds., Medpharm Scientific Publishers, Stuttgart, pp. 95-115, 1992. Large "carrier" particles (containing no drug) have been co-delivered with therapeutic aerosols to aid in achieving efficient aerosolization among other possible benefits. French, D. L., Edwards, D. A. and Niven, R. W., J. Aerosol Sci., 27:769-783 (1996).

Among the disadvantages of DPF's is that powders of fine particulates usually have poor flowability and aerosolization properties, leading to relatively low respirable fractions of aerosol, which are the fractions of inhaled aerosol that deposit in the lungs, escaping deposition in the mouth and throat. Gonda, I., in *Topics in Pharmaceutical Sciences*, (1991), D. Crommelin and K. Midha, Editors, Stuttgart: Medpharm Scientific Publishers, pp. 95-117 (1992). Poor flowability and aerosolization properties are typically caused by particulate aggregation, due to particle-particle interactions, such as hydrophobic, electrostatic, and capillary interactions. Some improvements in DPF's have been made. For example, dry powder formulations ("DPFs") with large particle size have been shown to possess improved flowability characteristics, such as less aggregation (Edwards, et al., Science 276:1868-1871 (1997)), easier aerosolization, and potentially less phagocytosis. Rudt, S, and R. H. Muller, J., Controlled Release, 22:263-272 (1992); Tabata, Y. and Y. Ikada, J. Biomed. Mater. Res., 22:837-858 (1988). An effective dry-powder inhalation therapy for both short and long term release of therapeutics, either for local or systemic delivery, requires a method to deliver a DPF to the lungs efficiently, and at therapeutic levels, without requiring excessive energy input.

Nebulizers, such as described by Cipolla et al. (Cipolla et al. Respiratory Drug Delivery VII, Biological, Pharmaceutical, Clinical and Regulatory Issues Relating to Optimized Drug Delivery by Aerosol, Conference held May 14-18, 2000, Palm Springs, Fla., the contents of which are incorporated herein by reference in their entirety), also are employed in pulmonary delivery.

Inhalation devices which can be employed to deliver dry powder formulations to the lungs include non-breath-activated or "multistep" devices. One such device is described in U.S. Pat. No. 5,997,848 issued to Patton et al. on Dec. 7, 1999, the entire teachings of which are incorporated herein by reference. In these devices, the drug formulation is first dispersed by energy independent of a patient's breath, then inhaled.

Inhalation devices that utilize a "single, breath-activated-step" are designed such that they disperse a powder which is immediately inhaled by a subject, i.e., in a single step, for example, a simple dry powder inhaler (see for example, U.S. Pat. Nos. 4,995,385 and 4,069,819).

Other examples of inhalers include but are not limited to the SPINHALER® (Fisons, Loughborough, U.K.) and ROTAHALER® (Glaxo-Wellcome, Research Triangle Park, N.C.).

In comparison to "single-step" inhalers, existing "multi-step inhalers" are more complex to operate and tend to be more costly since extra energy is needed to deliver a drug to the lungs. This amount of energy required increases with increasing drug mass. On the other hand, "high efficiency" of drug delivery to the respiratory tract, meaning about 50% of the drug mass initially contained in a drug receptacle, (i.e., the "nominal dose"), is typically only achieved with breath-activated, multi-step inhaler systems. Therefore, patients have until now needed to make a choice between cost/complexity and efficiency of drug delivery. The reason for this trade-off is that existing inhalation methodologies and devices are associated with inherent formulation inefficiencies and/or inherent device design limitations. Such inefficiencies result in unwanted drug loss and elevated overall cost of treatment. In addition, and often as a consequence, existing inhalation devices and methodologies can often fail to deliver to the lung a sufficient (e.g., therapeutic) mass of drug in a single breath. Currently, the amount of drug that can be delivered to the lung in a single breath, via liquid or dry powder inhalers, generally does not exceed 5 mg (Cipolla, et al., *Resp. Drug Delivery*, VII 2000:231-239 (2000)).

Therefore a need exists for delivering an agent to the pulmonary system wherein at least about 50% of the nominal dose of the agent is delivered to the pulmonary system via a single-step inhalation system. A need also exists for delivery of a relatively large mass of an agent, such as, for example, a therapeutic, prophylactic, diagnostic, or prognostic agent. A need also exists for delivery of a relatively large mass of a bioactive agent, in particular, a large mass of inhaled dry powder. A need further exists for methods of delivering to the pulmonary system, in a single step, from a simple breath-activated device, a single, high dose of an agent, such as a bioactive agent.

SUMMARY OF THE INVENTION

The invention is related to methods of delivery of an agent (for example, a therapeutic agent, a prophylactic agent, a diagnostic agent, a prognostic agent) to the pulmonary system. The invention is also related to methods of delivery of a bioactive agent to the pulmonary system.

In one embodiment, the invention is drawn to a method of delivering an agent to the pulmonary system, in a single, breath-activated step comprising: a) providing particles comprising an agent; and b) administering the particles, from a receptacle having a mass of the particles, to a subject's respiratory tract, wherein the particles deliver at least about 50% of the mass of particles.

In another embodiment, the invention is drawn to a method of delivering an agent to the pulmonary system, in a single, breath comprising: a) providing particles comprising an agent; and b) administering the particles, from a receptacle having a mass of the particles, to a subject's respiratory tract, wherein the particles deliver at least about 5 milligrams of an agent. In other embodiments, the particles deliver at least about 7 milligrams of an agent, at least about 10 milligrams of an agent, at least about 15 milligrams of an agent, at least about 20 milligrams of an agent or at least about 25 milligrams of an agent. Higher amounts of agent can also be delivered, for example, the particles can deliver at least about 35, at least about 40 or at least about 50 milligrams of an agent.

In another embodiment, the invention is drawn to a method of delivering an agent to the pulmonary system comprising: a) providing carrier particles having a tap density of less than 0.4 g/cm$^3$; b) providing a composition which comprises at least one agent; c) mixing the carrier particles in a) and the composition in b) to form a respirable composition; and d) administering the respirable composition in c) to the respiratory tract of a subject. As used herein, the term "respirable composition" refers to a composition which is suitable for delivery to the respiratory tract of a subject.

The invention is also drawn to respirable compositions which are capable of being delivered to the pulmonary system. The respirable compositions of the invention preferably include carrier particles having a tap density less than 0.4 g/cm$^3$ and a composition comprising an agent. In one embodiment, the carrier particles which are included in the respirable compositions can be prepared separately without an agent and then mixed with a composition containing an agent.

In one embodiment, the particles of the invention are administered from a receptacle having, holding, containing or enclosing a mass of particles. Receptacles which have a volume of at least about 0.37 cm$^3$ can be employed in the invention. Larger receptacles having a volume of at least about 0.48 cm$^3$, 0.67 cm$^3$ or 0.95 cm$^3$ can also be employed. The receptacles preferably have a design suitable for use in a dry powder inhaler.

In another embodiment, the energy holding the particles of the dry powder in an aggregated state is such that a patient's breath, over a reasonable physiological range of inhalation flow rates, is sufficient to deaggregate the powder contained in the receptacle into respirable particles. The deaggregated particles can penetrate via the patient's breath into and deposit in the airways and/or deep lung with high efficiency.

In a preferred embodiment of the invention, the particles have a tap density of less than about 0.4 g/cm$^3$, preferably around 0.1 g/cm$^3$ or less. In another embodiment, the particles have a mass median geometric diameter (MMGD) larger than 5 µm, preferably around about 10 µm or larger. In yet another embodiment, the particles have a mass median aerodynamic diameter (MMAD) ranging from about 1 µm to about 5 µm.

In one embodiment, the carrier particles have about a 10 micron diameter and a density of about 0.001 g/cm$^3$ and an aerodynamic diameter of about 0.3 microns, preferably about 0.001 to about 0.3 microns (about 10 to about 300 nanometers) or about 0.001 to about 0.2 microns. The carrier particles are not considered respirable in this range. Submicron particles are capable of conferring sufficient density to bring the non-respirable carrier particles into the respirable range. In one embodiment, the density of the submicron particles are, for example, about 1 g/cm$^3$. Such carrier particles are designed to ensure that a therapeutic amount of nanometer-sized agent would not adversely affect aerodynamic performance of the carrier particle when the agent is adhered to the surface, adsorbed on to the surface or chemically associated with the carrier particle. For example, to address this concern, carrier particles are designed with about a 10 µm diameter and a very low density (of about 0.001 g/cm$^3$) which by itself might produce particles with a much smaller aerodynamic size (for example, 0.3 µm) that fall below the 1-5 µm respirable range. However, upon inclusion of enough nanometer-sized submicron particles (for example, about 10-200 nm) which have a greater density (for example, about 1 g/cm$^3$) and comprise agent, the resulting particles would be engineered to fall within the size and porosity range required. In this way, larger loads of agent are accommodated. While not being bound to one explanation, it is believed that because of the small particle size of the micronized particles, the number of particle-particle contact points within a given volume is large relative to the powders made of larger particles. Powders with small particle size require large energies to be dispersed into an aerosol cloud. The effect of the large energy requirement of such powders is that both a large device and a small dose mass is necessary.

The invention has numerous advantages. For example, a large single dose of an agent (for example, a therapeutic agent, a prophylactic agent, a diagnostic agent, a prognostic agent) can be administered to the pulmonary system via a DPI with high efficiency. The invention employs a simple, cost-effective device for pulmonary delivery which increases efficiency and minimizes wasted drug. Since dosage frequency can be reduced by the delivery method of the invention, patient compliance to treatment or prophylaxis protocols is expected to improve. Pulmonary delivery advantageously can eliminate the need for injection. For example, the requirement for daily insulin injections can be avoided. Also, the enhancing properties of the particles themselves can result in a dose advantage where the amount of agent needed to achieve the therapeutic, prophylactic, diagnostic or prognostic effect is actually reduced. Examples 5-9 disclose such an effect with L-Dopa. This dose advantage can produce at least a 2-fold increase in bioavailability (for example, plasma level bioavailability) as well as in therapeutic advantages in comparison with other modes of administration, especially oral administration. Still further, the combination of a highly efficient delivery and a dose advantage potentiate an agent's effectiveness beyond presently known levels. Also, the fact that the particles can be used as carriers for a variety of agents underscores the broad applicability of the instant invention.

BRIEF DESCRIPTION OF THE DRAWINGS

FIG. 1 is a graph showing mass median geometric diameter (MMGD) in microns plotted against pressure for micronized albuterol sulfate (diamonds), spray-dried albuterol sulfate (squares) and spray-dried hGH (triangles).

FIG. 2A is a bar graph showing median geometric diameter of micronized albuterol sulfate, spray-dried albuterol sulfate and spray-dried hGH as primary particles (left bar of each pair), as measured by RODOS, compared to emitted particles (right bar of each pair) out of the inhaler at 30 L/min, as measured by IHA.

FIG. 2B is a bar graph showing median aerodynamic diameter of micronized albuterol sulfate and spray-dried albuterol sulfate as primary particles (left bar), as measured by a AeroDispenser, compared to emitted particles (right bar) out of the inhaler at 30 L/min, as measured by AeroBreather.

FIG. 3 is a bar graph showing the Fine Particle Fraction (FPF)>4.0 microns of the Emitted Dose Using DPI's at 60 L/min.

FIG. 4 is a bar graph showing a comparison of mass (left bar) and gamma count (right bar) particle size distributions of radio-labeled particles.

FIG. 5 is a graph showing the mass deposited in the lungs (diamonds) relative to the nominal dose (diamonds). The average deposition for the 10 individuals was 59% (dotted line).

FIG. 6 is a bar graph showing a comparison of mass fraction distributions obtained for 6 mg (left bar) and 50 mg (right bar) fill weights.

FIG. 7 is a graph showing the relative lung deposition of particles of the instant invention (circles) over a range of inspiratory flow rates in healthy volunteers. This is compared to lung deposition from dry powder inhalers (DPI's) (solid line) over the same range of inspiratory flow rates. For comparison to DPI's, deposition efficiency of the particles of the present invention were normalized to an average value of 1.0 (dotted line). The average efficiency of mass deposited in the lung divided by the nominal dose for particles of present invention is 59%, as represented in FIG. 5.

FIG. 8 is a plot representation showing plasma concentration of L-Dopa vs. time following oral or pulmonary administration (normalized for an 8 mg dose).

FIG. 9 is a plot representation showing plasma concentration of ketoprofen vs. time for oral and pulmonary groups.

FIG. 10 is a plot representation showing plasma concentration of ketoprofen vs. time for oral group.

FIG. 11 is a plasma concentration of ketoprofen vs. time for pulmonary group.

FIG. 12 is a plot showing RODOS curves for different powder formulations that include L-DOPA.

FIG. 13A and FIG. 13B are HPLC chromatograms that depict L-DOPA recovery from powders (FIG. 13A) compared to a blank sample (FIG. 13B).

FIG. 14A depicts L-DOPA plasma levels following pulmonary and oral routes.

FIG. 14B depicts L-DOPA plasma levels following pulmonary, oral and intravenous administration.

FIG. 15A and FIG. 15B show results, respectively, of oral and pulmonary L-DOPA on functional "placing task" in a rat model of Parkinson's disease.

FIG. 16A and FIG. 16B show results, respectively of oral and pulmonary L-DOPA on functional "bracing task" in a rat model of Parkinson's disease.

FIG. 17A and FIG. 17B show results, respectively of oral and pulmonary L-DOPA on a functional akinesia task in a rat model of Parkinson's disease.

FIG. 18 shows results of oral and pulmonary delivery of L-DOPA on functional rotation in a rat model of Parkinson's disease.

FIG. 19 shows the results of a methacholine challenge in a guinea pig model over a 24-hour period following treatment with Salmeterol formulations [F-1 (0.5), solid diamond; F-1 (1.0), solid square; F-1 (2.0) solid triangle] compared to SEREVENT® formulations [SX-1 (0.5) "x" and SX-2 (1.0) open circle].

FIG. 20 shows the results of a methacholine challenge in a guinea pig model over a 24-hour period following treatment with Salmeterol formulations [F-2 (0.5), solid diamond; F-2 (1.0), solid square; F-2 (2.0) solid triangle] compared to SEREVENT® formulations [SX-1 (0.5) "x" and SX-2 (1.0) open circle].

DETAILED DESCRIPTION OF THE INVENTION

The features and other details of the invention, either as steps of the invention or as combination of parts of the invention, will now be more particularly described with reference to the accompanying drawings and pointed out in the claims. It will be understood that the particular embodiments of the invention are shown by way of illustration and not as limitations of the invention. The principle feature of this invention may be employed in various embodiments without departing from the scope of the invention. This application also is related to U.S. Pat. No. 6,514,482, issued Feb. 4, 2003, entitled Pulmonary Delivery in Treating Disorders of the Central Nervous System and to its Continuation-in-Part application, U.S. Pat. No. 6,613,308, issued Sep. 2, 2003, with the same title and inventors filed on even date as the instant application. The entire teachings of said applications are incorporated in their entirety by reference herein.

The invention is related to methods of delivery to the pulmonary system of subject particles. The invention is also related to respirable compositions which comprise carrier particles and which are capable of being delivered to the pulmonary system.

In one embodiment, the particles of the invention comprise an agent. As used herein, the term "agent" includes, but is not limited to, therapeutic agents, prophylactic agents, diagnostic agents and prognostic agents. The invention is also related to agents which themselves comprise particles delivered by this method. Depending upon the intended use, the agent may be in the form of, but not limited to, a dry powder (for example, a particulate powder), particles (such as, but not limited to, micronized particles, submicron particles, nanometer-sized particles, liposomes, microspheres, microparticles, micelles, and beads), crystals, a liquid solution, a suspension or an emulsion. The term "agent" includes bioactive agents. As used herein, the term "bioactive" refers to having an effect on a living organism, for example, a mammal and in particular a human subject. Agents in the form of particles or particulate powders may be prepared by milling, filtering, evaporating, extracting, and spray drying as well as other techniques known to those skilled in the art. In one embodiment, the agent is non-crystalline, for example, the agent does not have a crystalline structure or does not comprise crystals.

Some examples of suitable bioactive agents include drugs (for example, hydrophobic drugs, hydrophilic drugs), pharmaceutical formulations, vitamins, pharmaceutical adjuvants, proteins, peptides, polypeptides, hormones, amino acids, nucleic acids, vaccine formulations, inactivated viruses, phospholipids, surfactants and any combinations thereof. Other examples of agents include synthetic compounds, inorganic compounds and organic compounds.

This invention also relates to the preparation of unique particles by spray drying. The unique properties of the particles which give them their excellent respirability, flowability and dispersibility are maintained whether the agent is (1) part of the spray-drying pre-mixture and thereby incorporated into the particles; (2) added to separately-prepared particles so that the agent is adhered onto or in chemical association with the particles; or (3) blended so that the agent is mixed with, and co-delivered with the particles. The chemical association includes, but is not limited to, ionic interactions, attraction of charged particles and/or agent, dipole-dipole interactions, Van der Waals forces, covalent interactions, adsorption and hydrogen bonding.

Unlike particles known in the art, the dry particles of the instant invention are versatile. For example, the particles of the invention can incorporate an agent, carry an agent or co-deliver an agent or any combination thereof. In one embodiment, the co-delivered particles may be described as escorts that accompany at least one agent to the desired deposition site in the lung. For example, lactose is an approved, commercially-available carrier. However, lactose cannot be efficiently delivered to the deep lung. The particles of the instant invention do reach the deep lung and are capable of escorting, accompanying and/or co-delivering the desired agent to its desired deposition site. Several examples are provided herein. In this respect, the particles of the instant invention, when used as carriers, have advantages and offer options that other carriers, including lactose, do not.

The particles of the invention are capable of carrying surprisingly high loads of agent. The particles of the invention are also highly dispersible and are capable of targeting regions in the respiratory system. Compositions used in the methods of the invention comprising dry particles carrying surprisingly high loads of agent are also capable of targeting to particular regions of the respiratory system, for example, upper airways, central airways and/or deep lung.

By considering the individual properties of the particles of the invention and agent, the compositions may be optimized for successful pulmonary administration. Compositions comprising highly-dispersible particles can optionally include additional particles and/or agents. It is understood that compositions comprising the particles of the invention include particles with or without agent. If present, the agent may be, among other things, (1) incorporated into the particles, (2) adsorbed, adhered onto or in chemical association with the particles, and/or (3) blended so that the agent is mixed with, and co-delivered with the particles.

As described herein, compositions comprising the particles of the invention, especially highly dispersible particles as defined herein, can further comprise an agent. In one embodiment, compositions comprising the particles of the invention comprise at least one additional agent. As indicated, the compositions comprising the particles of the invention can incorporate an agent in the particles, carry an agent with the particles and/or co-deliver an agent or any combination thereof. Examples of agents include, but are not limited to, therapeutic agents, prophylactic agents, diagnostic agents and prognostic agents. Suitable agents also include bioactive agents. Some examples of suitable bioactive agents include but are not limited to drugs (e.g., hydrophobic drugs, hydrophilic drugs), pharmaceutical formulations, vitamins, pharmaceutical adjuvants, proteins, peptides, polypeptides, hormones, amino acids, nucleic acids, vaccine formulations, inactivated viruses, lung surfactants and any combinations thereof. Other examples include synthetic compounds, inorganic compounds and organic compounds, proteins and peptides, polysaccharides and other sugars, lipids, and DNA and RNA nucleic acid sequences having therapeutic, prophylactic, diagnostic and/or prognostic activities. Nucleic acid sequences include genes, antisense molecules which bind to complementary DNA to inhibit transcription, and ribozymes. The drugs include hydrophobic and hydrophilic drugs.

Agents, including agents incorporated into, adhered onto, in chemical association with, and/or blended and co-delivered with the particles of the invention can have a variety of biological activities. Such agents include, but are not limited to, vasoactive agents, neuroactive agents, hormones, anticoagulants, immunomodulating agents, cytotoxic agents, prophylactic agents, antibiotics, antiviral agents, antisense agents, antigens, and antibodies, such as, for example, monoclonal antibodies, e.g., palivizumab (Medimmune, Gaithersberg, Md.). In some instances, the proteins may be antibodies or antigens which otherwise would have to be administered by injection to elicit an appropriate response. Compounds with a wide range of molecular weight can be encapsulated, for example, between 100 and 500,000 Daltons. Proteins are defined herein as consisting of 100 amino acid residues or more; peptides are less than 100 amino acid residues. Unless otherwise stated, the term protein refers to both proteins and peptides. Examples include insulin and other hormones. Polysaccharides, such as heparin, can also be administered.

The particles, especially the highly dispersible particles described herein, may include a bioactive agent suitable for systemic treatment. Alternatively, the particles can include a bioactive agent for local delivery within the lung, such as, for example, agents for the treatment of asthma, emphysema, or cystic fibrosis, or for systemic treatment. For example, genes for the treatment of diseases such as cystic fibrosis can be administered, as can beta agonists for asthma. Other specific bioactive agents include, but are not limited to, growth hormone (e.g., mammalian growth hormone, in particular human growth hormone), interleukins, insulin, calcitonin, luteinizing hormone releasing hormone ("LHRH") or gonadotropin-releasing hormone ("LHRH") and analogs thereof (e.g. leoprolide), granulocyte colony-stimulating factor ("G-CSF"), parathyroid hormone-related peptide, somatostatin, testosterone, progesterone, estradiol, nicotine, fentanyl, norethisterone, clonidine, scopolamine, salicylate, cromolyn sodium, salmeterol, formeterol, ipratropium bromide, albuterol (including albuterol sulfate), fluticasone, valium, alprazolam and levodopa (L-Dopa). Other suitable therapeutic and/or prophylatic agents include, but are not limited to those listed in U.S. Pat. No. 5,875,776, and U.S. Pat. No. 6,514,482, the entire teachings of which are incorporated herein by reference. Those therapeutic agents which are charged, such as most of the proteins, including insulin, can be administered as a complex between the charged agent and a molecule of opposite charge. Preferably, the molecule of opposite charge is a charged lipid or an oppositely-charged protein. The particles can incorporate substances such as lipids which allow for the sustained release of small and large molecules. Addition of these complexes or substances is applicable to particles of any size and shape, and is especially useful for altering the rate of release of therapeutic agents from inhaled particles.

Any of a variety of diagnostic and/or prognostic agents can be incorporated within the highly dispersible particles, which can locally or systemically deliver the incorporated agents, following administration to a patient. Alternatively, diagnostic and/or prognostic agents can be carried with, adhered onto, chemically-associated with, and/or co-delivered with the highly dispersible particles of the invention. Particles incorporating diagnostic agents can be detected using standard techniques available in the art and commercially available equipment.

In one embodiment, a composition comprising the particles of the invention further comprises a diagnostic and/or prognostic agent. The diagnostic and/or prognostic agent can comprise a label, including, but not limited to, a radioisotope, an epitope label, an affinity label, a spin label, an enzyme label, a fluorescent group and a chemiluminescent group. In one embodiment, the label is a radioisotope, for example, $^{99m}$Tc. It is understood that additional labels are well known in the art and are encompassed by the present invention.

Any biocompatible or pharmacologically acceptable gas, for example, can be incorporated into the particles or trapped in the pores of the particles using technology known to those skilled in the art. The term gas refers to any compound which is a gas or is capable of forming a gas at the temperature at which imaging is being performed. In one embodiment, retention of gas in the particles is improved by forming a gas-impermeable barrier around the particles. Such barriers are well known to those of skill in the art.

Other imaging agents which may be utilized include commercially available agents used in positron emission tomography (PET), computer-assisted tomography (CAT), single photon emission computerized tomography, x-ray, fluoroscopy, and magnetic resonance imaging (MRI).

Examples of suitable materials for use as contrast agents in MRI include gadolinium chelates, such as diethylene triamine pentacetic acid (DTPA) and gadopentotate dimeglumine, as well as iron, magnesium, manganese, copper and chromium.

Examples of materials useful for CAT and x-rays include iodine-based materials for intravenous administration, such as ionic monomers typified by diatrizoate and iothalamate, non-ionic monomers such as iopamidol, isohexyl, and ioversol, non-ionic dimers, such as iotrol and iodixanol, and ionic dimers, for example, ioxagalte.

Agents also include targeting molecules which can be attached to the particles via reactive functional groups on the particles. Targeting molecules permit binding interaction of the particle with specific receptor sites, such as those within the lungs. The particles can be targeted by attachment of ligands which specifically or non-specifically bind to particular targets. Exemplary targeting molecules include antibodies (e.g., polyclonal sera, monoclonal, chimeric, humanized, human) and fragments thereof (e.g., Fab, Fab', F(ab')$_2$, Fv), including antibody variable regions, lectins, and hormones or other organic molecules capable of specific binding, for example, to receptors on the surfaces of the target cells.

Agents, and in particular bioactive agents, can also include surfactants, such as surfactants which are endogenous to the lung. Both naturally-occurring and synthetic lung surfactants are encompassed in the scope of the invention.

The methods of the invention also relate to administering to the respiratory tract of a subject, particles and/or compositions comprising the particles of the invention, which can be enclosed in a receptacle. As described herein, in certain embodiments, the invention is drawn to methods of delivering the particles of the invention, while in other embodiments, the invention is drawn to methods of delivering respirable compositions comprising the particles of the invention. As used herein, the term "receptacle" includes but is not limited to, for example, a capsule, blister, film covered container well, chamber and other suitable means of storing particles, a powder or a respirable composition in an inhalation device known to those skilled in the art.

In a preferred embodiment, the receptacle is used in a dry powder inhaler. Examples of dry powder inhalers that can be employed in the methods of the invention include but are not limited to, the inhalers disclosed is U.S. Pat. Nos. 4,995,385 and 4,069,819, the SPINHALER® (Fisons, Loughborough, U.K.), ROTAHALER® (Glaxo-Wellcome, Research Triangle Technology Park, North Carolina), FLOWCAPS® (Hovione, Loures, Portugal), INHALATOR® (Boehringer-Ingelheim, Germany), and the AEROLIZER® (Novartis, Switzerland), the Diskhaler (Glaxo-Wellcome, RTP, NC) and others known to those skilled in the art. In one embodiment, the inhaler employed is described in U.S. patent application, entitled Inhalation Device and Method, by David A. Edwards, et al., filed on Apr. 16, 2001 under Ser. No. 09/835,302. The entire contents of this application are incorporated by reference herein.

In one embodiment, the volume of the receptacle is at least about 0.37 cm$^3$. In another embodiment, the volume of the receptacle is at least about 0.48 cm$^3$. In yet another embodiment, are receptacles having a volume of at least about 0.67 cm$^3$ or 0.95 cm$^3$. The invention is also drawn to receptacles which are capsules, for example, capsules designated with a particular capsule size, such as 2, 1, 0, 00 or 000. Suitable capsules can be obtained, for example, from Shionogi (Rockville, Md.). Blisters can be obtained, for example, from Hueck Foils, (Wall, N.J.). Other receptacles and other volumes thereof suitable for use in the instant invention are known to those skilled in the art.

The receptacle encloses or stores particles and/or respirable compositions comprising particles. In one embodiment, the particles and/or respirable compositions comprising particles are in the form of a powder. The receptacle is filled with particles and/or compositions comprising particles, as known in the art. For example, vacuum filling or tamping technologies may be used. Generally, filling the receptacle with powder can be carried out by methods known in the art. In one embodiment of the invention, the particles, powder or respirable composition which is enclosed or stored in a receptacle has a mass of at least about 5 milligrams. Preferably, the mass of the particles or respirable compositions stored or enclosed in the receptacle is at least about 10 milligrams.

In one embodiment of the invention, the receptacle encloses a mass of particles, especially a mass of highly dispersible particles as described herein. The mass of particles comprises a nominal dose of an agent. As used herein, the phrase "nominal dose" means the total mass of an agent which is present in the mass of particles in the receptacle and represents the maximum amount of agent available for administration in a single breath.

Particles and/or respirable compositions comprising particles are stored or enclosed in the receptacles and are administered to the respiratory tract of a subject. As used herein, the terms "administration" or "administering" of particles and/or respirable compositions refer to introducing particles to the respiratory tract of a subject.

As described herein, in one embodiment, the invention is drawn to a respirable composition comprising carrier particles and an agent. In another embodiment, the invention is drawn to a method of delivering a respirable composition comprising carrier particles and an agent. As used herein, the term "carrier particle" refers to particles which may or may not comprise an agent, and aid in delivery of an agent to a subject's respiratory system, for example, by increasing the stability, dispersibility, aerosolization, consistency and/or bulking characteristics of an agent. It is clear that in certain embodiments, the particles of the invention are carrier particles which are capable of being delivered to the respiratory tract of a subject.

In one embodiment, the invention is drawn to a respirable composition which is formed from the blending or mixing of carrier particles (without an agent) with a composition comprising an agent. This respirable composition can then be administered to the respiratory tract of a subject. In another embodiment, the respirable composition is delivered to a subject's respiratory system, for example, through the use of a dry powder inhaler device. In one embodiment, the respirable composition comprises a composition which includes an agent which is in the form of micronized particles (e.g., submicron particles).

In embodiments where the particles of the invention are carrier particles which are co-administered with an agent, the carrier particles preferably enhance delivery of the agent to a subject's respiratory system (e.g., upper airways, lower airways, deep lungs). In one embodiment, the particles of the invention are carrier particles which are co-administered with an agent and enhance uniform delivery of the agent to a particular region of a subject's respiratory system (for example, the upper airways, central airways, or preferably the deep lungs). Co-administration of the carrier particles of the invention with an agent may also help reduce phagocytosis of the agent by macrophages (for example, alveolar macrophages) and/or increase the dispersibility and aerosolization of the agent (for example, by decreasing particle aggregation or agglomeration).

As described herein, the particles and respirable compositions comprising the particles of the invention may optionally include a surfactant, such as a surfactant which is endogenous to the lung. The particles and respirable compositions comprising the particles of the invention described herein are also preferably biodegradable and biocompatible, and optionally are capable of affecting the biodegradability and/or the rate of delivery of a co-administered agent.

As described herein, the particles, including the carrier particles contained in the respirable compositions described herein, are preferably "aerodynamically light". As described below, "aerodynamically light", as used herein, refers to particles having a tap density of less than 0.4 $g/cm^3$. In one embodiment, the carrier particles have a tap density of near to or less than about 0.1 $g/cm^3$. Further descriptions of tap density and methods of measuring tap density are described in greater detail below.

In one embodiment, the particles, including the carrier particles contained in the respirable compositions described herein, preferably have a mass median geometric diameter (MMGD) greater than about 5 µm. In other embodiments, the particles have a MMGD greater than about 5 µm and ranging to about 30 µm or a MMGD ranging from about 10 µm to about 30 µm. Further descriptions of MMGD and methods for calculating the MMGD of the particles are described in greater detail below.

It is understood that the particles and/or respirable compositions comprising the particles of the invention which can be administered to the respiratory tract of a subject can also optionally include pharmaceutically-acceptable carriers, as are well known in the art. The term "pharmaceutically-acceptable carrier" as used herein, refers to a carrier which can be administered to a patient's respiratory system without any significant adverse toxicological effects. Appropriate pharmaceutically-acceptable carriers, include those typically used for inhalation therapy (e.g., lactose) and include pharmaceutically-acceptable carriers in the form of a liquid (e.g., saline) or a powder (e.g., a particulate powder). In one embodiment, the pharmaceutically-acceptable carrier comprises particles which have a mean diameter ranging from about 50 µm to about 200 µm, and in particular lactose particles in this range. It is understood that those of skill in the art can readily determine appropriate pharmaceutically-acceptable carriers for use in administering, accompanying and or co-delivering the particles of the invention.

In one embodiment of the invention, the particles and/or respirable compositions comprising particles, are administered in a single, breath-activated step. As used herein, the phrases "breath-activated" and "breath-actuated" are used interchangeably. As used herein, "a single, breath-activated step" means that particles are dispersed and inhaled in one step. For example, in single, breath-activated inhalation devices, the energy of the subject's inhalation both disperses particles and draws them into the oral or nasopharyngeal cavity. Suitable inhalers which are single, breath-actuated inhalers that can be employed in the methods of the invention include but are not limited to simple, dry powder inhalers disclosed in U.S. Pat. Nos. 4,995,385 and 4,069,819, the SPINHALER® (Fisons, Loughborough, U.K.), ROTAHALER® (Glaxo-Wellcome, Research Triangle Technology Park, North Carolina), FLOWCAPS® (Hovione, Loures, Portugal), INHALATOR® (Boehringer-Ingelheim, Germany), and the AEROLIZER® (Novartis, Switzerland), the Diskhaler (Glaxo-Wellcome, RTP, NC) and others, such as known to those skilled in the art. In one embodiment, the inhaler employed is described in U.S. patent application, entitled Inhalation Device and Method, by David A. Edwards, et al., filed on Apr. 16, 2001, under Ser. No. 09/835,302. The entire contents of this application are incorporated by reference herein.

"Single breath" administration can include single, breath-activated administration, but also administration during which the particles, respirable compositions or powders are first dispersed, followed by the inhalation or inspiration of the dispersed particles, respirable compositions or powders. In the latter mode of administration, additional energy than the energy supplied by the subject's inhalation disperses the particles. An example of a single breath inhaler which employs energy other than the energy generated by the patient's inhalation is the device described in U.S. Pat. No. 5,997,848 issued to Patton et al. on Dec. 7, 1999, the entire teachings of which are incorporated herein by reference.

In a preferred embodiment, the receptacle enclosing the particles, respirable compositions comprising particles or powder is emptied in a single, breath-activated step. In another preferred embodiment, the receptacle enclosing the particles is emptied in a single inhalation. As used herein, the term "emptied" means that at least 50% of the particle mass enclosed in the receptacle is emitted from the inhaler during administration of the particles to a subject's respiratory system.

In a preferred embodiment of the invention, the particles administered are highly dispersible. As used herein, the phrase "highly dispersible" particles or powders refers to particles or powders which can be dispersed by a RODOS dry powder disperser (or equivalent technique) such that at about 1 Bar, particles of the dry powder emit from the RODOS orifice with geometric diameters, as measured by a HELOS or other laser diffraction system, that are less than about 1.5 times the geometric particle size as measured at 4 Bar. Highly dispersible powders have a low tendency to agglomerate, aggregate or clump together and/or, if agglomerated, aggregated or clumped together, are easily dispersed or de-agglomerated as they emit from an inhaler and are breathed in by the subject. Typically, the highly dispersible particles suitable in the methods of the invention display very low aggregation compared to standard micronized powders which have similar aerodynamic diameters and which are suitable for delivery to the pulmonary system. Properties that enhance dispersibility include, for example, particle charge, surface roughness, surface chemistry and relatively large geometric diameters. In one embodiment, because the attractive forces between particles of a powder varies (for constant powder mass) inversely with the square of the geometric diameter and the shear force seen by a particle increases with the square of the geometric diameter, the ease of dispersibility of a powder is on the order of the inverse of the geometric diameter raised to the fourth power. The increased particle size diminishes interparticle adhesion forces (Visser, J., *Powder Technology,* 58:1-10 (1989)). Thus, large particle size, all other things equivalent, increases efficiency of aerosolization to the lungs for particles of low envelope mass density. Increased surface irregularities, and roughness also can enhance particle dispersibility. Surface roughness can be expressed, for example by rugosity.

The particles preferably are biodegradable and biocompatible, and optionally are capable of biodegrading at a controlled rate for delivery of a therapeutic, prophylactic, diagnostic agent or prognostic agent. In addition to an agent, preferably a bioactive agent, the particles can further include a variety of materials. Both inorganic and organic materials can be used. For example, ceramics may be used. Fatty acids may also be used to form aerodynamically light particles. Other suitable materials include, but are not limited to, amino acids, gelatin, polyethylene glycol, trehalose, lactose, and dextran. Preferred particle compositions are further described below. In one embodiment, the particles of the invention are non-polymeric. In another embodiment, respirable compositions include carrier particles which are non-polymeric.

In one embodiment of the invention, particles administered to a subject's respiratory tract have a tap density of less than about 0.4 g/$cm^3$. Particles having a tap density of less than about 0.4 g/$cm^3$ are referred to herein as "aerodynamically light". In a preferred embodiment, the particles have a tap density of near to or less than about 0.1 g/$cm^3$. Tap density is a measure of the envelope mass density characterizing a particle. The envelope mass density of a particle of a statistically isotropic shape is defined as the mass of the particle divided by the minimum sphere envelope volume within which it can be enclosed. Features which can contribute to low tap density include irregular surface texture and hollow or porous structure.

Tap density can be measured by using instruments known to those skilled in the art such as the Dual Platform Microprocessor Controlled Tap Density Tester (Vankel, N.C.). Tap density is a standard measure of the envelope mass density. Tap density can be determined using the method of USP Bulk Density and Tapped Density, United States Pharmacopia convention, Rockville, Md., $10^{th}$ Supplement, 4950-4951, 1999. In another embodiment, the particles have a mass median geometric diameter (MMGD) greater than about 5 μm and preferably near to or greater than about 10 μm. In one embodiment, the particles have a MMGD greater than about 5 μm and ranging to about 30 μm. In another embodiment, the particles have a MMGD ranging from about 10 μm to about 30 μm.

In one embodiment, compositions comprising the particles of the instant invention have a dynamic bulk density of 0.1 g/$cm^3$ or greater and a tap density of less than about 0.4 g/$cm^3$. In a preferred embodiment, the particles have a dynamic bulk density of greater than 0.1 g/$cm^3$ and a tap density of near to or less than about 0.1 g/$cm^3$.

The MMGD of the particles can be measured using an electrical zone sensing instrument such as Coulter Multisizer IIe (Coulter Electronics, Luton, Beds, England) or a laser diffraction instrument (for example Helos, Sympatec, Inc., Princeton, N.J.). The diameter of particles in a sample will range depending upon factors such as particle composition and methods of synthesis. The distribution of size of particles in a sample can be selected to permit optimal deposition within targeted sites within the respiratory tract.

The aerodynamically light particles suitable for use in the instant invention may be fabricated or separated, for example by filtration or centrifugation, to provide a particle sample with a preselected size distribution. For example, greater than 30%, 50%, 70%, or 80% of the particles in a sample can have a diameter within a selected range of at least 5 μm. The selected range within which a certain percentage of the particles must fall may be for example, between about 5 and 30 μm, or optionally between 5 and 15 μm. In one embodiment, at least a portion of the particles have a diameter between about 9 and 11 μm. Optionally, the particle sample also can be fabricated wherein at least 90%, or optionally 95% or 99% of the particles, have a diameter within the selected range. The presence of the higher proportion of the aerodynamically light, larger diameter (at least about 5 μm) particles in the particle sample enhances the delivery of therapeutic prophylactic, diagnostic or prognostic agents which are incorporated into, carried with, adhered to the surface, adsorbed to the surface and/or co-delivered with, the particles to the deep lung.

In one embodiment, in the particle sample, the interquartile range may be 2 μm, with a mean diameter for example, between about 7.5 and 13.5 μm. Thus, for example, between at least 30% and 40% of the particles may have diameters within the selected range. Preferably, the said percentages of particles have diameters within a 1 μm range, for example, between 6.0 and 7.0 μm, 10.0 and 11.0 μm or 13.0 and 14.0 μm.

In a further embodiment, the particles have an aerodynamic diameter ranging from about 1 μm to about 5 μm. The aerodynamic diameter, $d_{aer}$, can be calculated from the equation:

$$d_{aer} = d_g \sqrt{\rho_{tap}}$$

where $d_g$ is the geometric diameter, for example the MMGD and ρ is the powder density. Experimentally, aerodynamic diameter can be determined by employing a gravitational settling method, whereby the time for an ensemble of particles to settle a certain distance is used to directly infer the aerodynamic diameter of the particles. An indirect method for measuring the mass median aerodynamic diameter (MMAD) is the multi-stage liquid impinger (MSLI).

In one embodiment, the particles of the invention have a dynamic bulk density greater than 0.1 g/cm$^3$.

In one embodiment of the invention, at least 50% of the mass of the particles stored in a receptacle are delivered to a subject's respiratory tract in a single, breath-activated step. Preferably, at least 55% of the mass of particles is delivered.

In another embodiment of the invention, at least 5 milligrams and preferably at least 7 milligrams or at least 10 milligrams of agent, preferably a bioactive agent, is delivered by administering, in a single breath, to a subject's respiratory tract particles enclosed in the receptacle. Amounts of at least 15, preferably of at least 20 and more preferably of at least 25, 30, 35, 40 and 50 milligrams can be delivered. In a preferred embodiment, amounts of at least 35 milligrams are delivered. In another preferred embodiment, amounts of at least 50 milligrams are delivered.

Particles administered to the respiratory tract of the subject are delivered to the pulmonary system. Particles suitable for use in the methods of the invention can travel through the upper airways (oropharynx and larynx), the lower airways which include the trachea followed by bifurcations into the bronchi and bronchioli and through the terminal bronchioli which in turn divide into respiratory bronchioli leading then to the ultimate respiratory zone, the alveoli or the deep lung. In one embodiment of the invention, most of the mass of particles deposit in the deep lung. In another embodiment of the invention, delivery is primarily to the central airways. In another embodiment, delivery is to the upper airways.

The particles suitable for use in the instant invention may be fabricated with the appropriate material, surface roughness, diameter and tap density for localized delivery to selected regions of the respiratory tract such as the deep lung, central or upper airways. For example, higher density or larger particles may be used for upper airway delivery, or a mixture of different-sized particles in a sample, provided with the same or a different agent may be administered to target different regions of the lung in one administration. Particles with degradation and release times ranging from seconds to months can be designed and fabricated, based on factors such as the particle material.

Delivery to the pulmonary system of particles in a single, breath-actuated step is enhanced by employing particles which are dispersed at relatively low energies, such as, for example, at energies typically supplied by a subject's inhalation. Such energies are referred to herein as "low". As used herein, "low energy administration" refers to administration wherein the energy applied to disperse and inhale the particles is in the range typically supplied by a subject during inhaling.

In one embodiment of the invention, highly dispersible particles which are administered to a subject comprise a bioactive agent and a biocompatible, and preferably biodegradable polymer, copolymer, or blend. The polymers may be tailored to optimize different characteristics of the particles including: i) interactions between the agent to be delivered and the polymer to provide stabilization of the agent and retention of activity upon delivery; ii) rate of polymer degradation and, thereby, rate of drug release profiles; iii) surface characteristics and targeting capabilities via chemical modification; and iv) particle porosity.

Surface eroding polymers such as polyanhydrides may be used to form particles. For example, polyanhydrides such as poly[(p-carboxyphenoxy)-hexane anhydride] (PCPH) may be used. Biodegradable polyanhydrides are described in U.S. Pat. No. 4,857,311. Bulk eroding polymers such as those based on polyesters including poly(hydroxy acids) also can be used. For example, polyglycolic acid (PGA), polylactic acid (PLA), or copolymers thereof may be used to form the particles. The polyester may also have a charged or functionalizable group, such as an amino acid. In a preferred embodiment, particles with controlled release properties can be formed of poly(D,L-lactic acid) and/or poly(D,L-lactic-co-glycolic acid) ("PLGA") which incorporate a surfactant such as dipalmitoyl phosphatidylcholine (DPPC).

Other polymers include polyamides, polycarbonates, polyalkylenes such as polyethylene, polypropylene, poly(ethylene glycol), poly(ethylene oxide), poly(ethylene terephthalate), poly vinyl compounds such as polyvinyl alcohols, polyvinyl ethers, and polyvinyl esters, polymers of acrylic and methacrylic acids, celluloses and other polysaccharides, and peptides or proteins, or copolymers or blends thereof. Polymers may be selected with or modified to have the appropriate stability and degradation rates in vivo for different controlled drug delivery applications.

Highly dispersible particles can be formed from functionalized polyester graft copolymers, as described in Hrkach et al., *Macromolecules*, 28:4736-4739 (1995); and Hrkach et al., "Poly(L-Lactic acid-co-amino acid) Graft Copolymers: A Class of Functional Biodegradable Biomaterials," *Hydrogels and Biodegradable Polymers for Bioapplications*, ACS Symposium Series No. 627, Raphael M. Ottenbrite et al., Eds., American Chemical Society, Chapter 8, pp. 93-101, 1996.

In a preferred embodiment of the invention, highly dispersible particles including a bioactive agent and a phospholipid are administered. Examples of suitable phospholipids include, among others, those listed in U.S. Pat. No. 6,514,482 described above. Other suitable phospholipids include phosphatidylcholines, phosphatidylethanolamines, phosphatidylglycerols, phosphatidylserines, phosphatidylinositols and combinations thereof. Specific examples of phospholipids include but are not limited to phosphatidylcholines dipalmitoyl phosphatidylcholine (DPPC), dipalmitoyl phosphatidylethanolamine (DPPE), distearoyl phosphatidylcholine (DSPC), dipalmitoyl phosphatidyl glycerol (DPPG) or any combination thereof. Other phospholipids are known to those skilled in the art. In a preferred embodiment, the phospholipids are endogenous to the lung.

The phospholipid, can be present in the particles in an amount ranging from about 0 to about 90 weight %. More commonly it can be present in the particles in an amount ranging from about 10 to about 60 weight %.

In another embodiment of the invention, the phospholipids or combinations thereof are selected to impart controlled release properties to the highly dispersible particles. The phase transition temperature of a specific phospholipid can be below, around or above the physiological body temperature of a patient. Preferred phase transition temperatures range from 30° C. to 50° C., (e.g., within ±10° C. of the normal body temperature of patient). By selecting phospholipids or combinations of phospholipids according to their phase transition temperature, the particles can be tailored to have controlled release properties. For example, by administering particles which include a phospholipid or combination of phospholipids which have a phase transition temperature higher than the patient's body temperature, the release of dopamine precursor, agonist or any combination of precursors and/or agonists can be slowed down. On the other hand, rapid release can be obtained by including in the particles phospholipids having lower transition temperatures. Particles having controlled release properties and methods of modulating release of a biologically active agent are described in U.S. Provisional Patent Application No. 60/150,742 entitled Modulation of Release from Dry Powder Formulations by Controlling Matrix Transition, filed on Aug. 25, 1999, the contents of which are incorporated herein in their entirety.

In another embodiment of the invention the particles can include a surfactant. As used herein, the term "surfactant" refers to any agent, which preferentially absorbs to an interface between two immiscible phases, such as the interface between water and an organic polymer solution, a water/air interface or organic solvent/air interface. Surfactants generally possess a hydrophilic moiety and a lipophilic moiety, such that, upon absorbing to microparticles, they tend to present moieties to the external environment that do not attract similarly-coated particles, thus reducing particle agglomeration.

In addition to lung surfactants, such as, for example, phospholipids discussed above, suitable surfactants include but are not limited to hexadecanol; fatty alcohols such as polyethylene glycol (PEG); polyoxyethylene-9-lauryl ether; a surface active fatty acid, such as palmitic acid or oleic acid; glycocholate; surfactin; a poloxomer; a sorbitan fatty acid ester such as sorbitan trioleate (Span 85); and tyloxapol.

The surfactant can be present in the particles in an amount ranging from about 0 to about 90 weight %. Preferably, it can be present in the particles in an amount ranging from about 10 to about 60 weight %.

Methods of preparing and administering particles which are aerodynamically light and include surfactants, and, in particular phospholipids, are disclosed in U.S. Pat. No. 5,855,913, issued on Jan. 5, 1999 to Hanes et al. and in U.S. Pat. No. 5,985,309, issued on Nov. 16, 1999 to Edwards et al. The teachings of both are incorporated herein by reference in their entirety. Methods of administering particles to patients in acute distress are disclosed. The highly dispersible particles being administered in the instant invention are capable of being delivered to the lung and absorbed into the system when other conventional means of delivering drugs fail.

In yet another embodiment, highly dispersible particles only including a bioactive agent and surfactant are administered. Highly dispersible particles may be formed of the surfactant and include a therapeutic prophylactic, or diagnostic agent, to improve aerosolization efficiency due to reduced particle surface interactions, and to potentially reduce loss of the agent due to phagocytosis by alveolar macrophages.

In another embodiment of the invention, highly dispersible particles including an amino acid are administered. Hydrophobic amino acids are preferred. Suitable amino acids include naturally occurring and non-naturally occurring hydrophobic amino acids. Some naturally occurring hydrophobic amino acids, including but not limited to, non-naturally occurring amino acids include, for example, beta-amino acids. Both D, L and racemic configurations of hydrophobic amino acids can be employed. Suitable hydrophobic amino acids can also include amino acid analogs. As used herein, an amino acid analog includes the D or L configuration of an amino acid having the following formula: —NH—CHR—CO—, wherein R is an aliphatic group, a substituted aliphatic group, a benzyl group, a substituted benzyl group, an aromatic group or a substituted aromatic group and wherein R does not correspond to the side chain of a naturally-occurring amino acid. As used herein, aliphatic groups include straight chained, branched or cyclic C1-C8 hydrocarbons which are completely saturated, which contain one or two heteroatoms such as nitrogen, oxygen or sulfur and/or which contain one or more units of desaturation. Aromatic groups include carbocyclic aromatic groups such as phenyl and naphthyl and heterocyclic aromatic groups such as imidazolyl, indolyl, thienyl, furanyl, pyridyl, pyranyl, oxazolyl, benzothienyl, benzofuranyl, quinolinyl, isoquinolinyl and acridintyl.

Suitable substituents on an aliphatic, aromatic or benzyl group include —OH, halogen (—Br, —Cl, —I and —F), —O(aliphatic, substituted aliphatic, benzyl, substituted benzyl, aryl or substituted aryl group), —CN, —NO$_2$, —COOH, —NH$_2$, —NH(aliphatic group, substituted aliphatic, benzyl, substituted benzyl, aryl or substituted aryl group), —N(aliphatic group, substituted aliphatic, benzyl, substituted benzyl, aryl or substituted aryl group)$_2$, —COO(aliphatic group, substituted aliphatic, benzyl, substituted benzyl, aryl or substituted aryl group), —CONH$_2$, —CONH(aliphatic, substituted aliphatic group, benzyl, substituted benzyl, aryl or substituted aryl group), —SH, —S(aliphatic, substituted aliphatic, benzyl, substituted benzyl, aromatic or substituted aromatic group) and —NH—C(=NH)—NH$_2$. A substituted benzylic or aromatic group can also have an aliphatic or substituted aliphatic group as a substituent. A substituted aliphatic group can also have a benzyl, substituted benzyl, aryl or substituted aryl group as a substituent. A substituted aliphatic, substituted aromatic or substituted benzyl group can have one or more substituents. Modifying an amino acid substituent can increase, for example, the lypophilicity or hydrophobicity of natural amino acids which are hydrophilic.

A number of the suitable amino acids, amino acids analogs and salts thereof can be obtained commercially. Others can be synthesized by methods known in the art. Synthetic techniques are described, for example, in Green and Wuts, "*Protecting Groups in Organic Synthesis*", John Wiley and Sons, Chapters 5 and 7, 1991.

Hydrophobicity is generally defined with respect to the partition of an amino acid between a nonpolar solvent and water. Hydrophobic amino acids are those acids which show a preference for the nonpolar solvent. Relative hydrophobicity of amino acids can be expressed on a hydrophobicity scale on which glycine has the value 0.5. On such a scale, amino acids which have a preference for water have values below 0.5 and those that have a preference for nonpolar solvents have a value above 0.5. As used herein, the term hydrophobic amino acid refers to an amino acid that, on the hydrophobicity scale, has a value greater or equal to 0.5, in other words, has a tendency to partition in the nonpolar acid which is at least equal to that of glycine.

Examples of amino acids which can be employed include, but are not limited to: glycine, proline, alanine, cysteine, methionine, valine, leucine, tyrosine, isoleucine, phenylalanine, tryptophan. Preferred hydrophobic amino acids include leucine, isoleucine, alanine, valine, phenylalanine and glycine. Combinations of hydrophobic amino acids can also be employed. Furthermore, combinations of hydrophobic and hydrophilic (preferentially partitioning in water) amino acids, where the overall combination is hydrophobic, can also be employed.

The amino acid can be present in the particles of the invention in an amount of at least 10 weight %. Preferably, the amino acid can be present in the particles in an amount ranging from about 20 to about 80 weight %. The salt of a hydrophobic amino acid can be present in the particles of the invention in an amount of at least 10 weight percent. Preferably, the amino acid salt is present in the particles in an amount ranging from about 20 to about 80 weight %. In preferred embodiments the particles have a tap density of less than about 0.4 g/cm$^3$.

Methods of forming and delivering particles which include an amino acid are described in U.S. Pat. No. 6,586,008, filed on Aug. 25, 1999, entitled, "Use of Simple Amino Acids to Form Porous Particles During Spray Drying," the teachings of which are incorporated herein by reference in their entirety.

The particles of the invention can also include excipients such as one or more of the following; a sugar, such as lactose, a protein, such as albumin, cholesterol and/or a surfactant.

If the agent to be delivered is negatively charged (such as insulin), protamine or other positively charged molecules can be added to provide a lipophilic complex which results in the sustained release of the negatively charged agent. Negatively charged molecules can be used to render insoluble positively charged agents.

Highly dispersible particles suitable for use in the methods of the invention may be prepared using single and double emulsion solvent evaporation, spray drying, solvent extraction, solvent evaporation, phase separation, simple and complex coacervation, interfacial polymerization, supercritical carbon dioxide ($CO_2$) and other methods well known to those of ordinary skill in the art. Particles may be made using methods for making microspheres or microcapsules known in the art, provided that the conditions are optimized for forming particles with the desired aerodynamic properties (e.g., aerodynamic diameter) or additional steps are performed to select particles with the density and diameter sufficient to provide the particles with an aerodynamic diameter between one and five microns, preferably between one and three microns.

With some polymeric systems, polymeric particles prepared using a single or double emulsion technique, vary in size depending on the size of the droplets. If droplets in water-in-oil emulsions are not of a suitably small size to form particles with the desired size range, smaller droplets can be prepared, for example, by sonication or homogenization of the emulsion, or by the addition of surfactants.

If the particles prepared by any of the above methods have a size range outside of the desired range, particles can be sized, for example, using a sieve, and further separated according to density using techniques known to those of skill in the art.

The particles are preferably prepared by spray drying.

The following equipment and reagents are referred to herein and for convenience will be listed once with the pertinent information. Unless otherwise indicated, all equipment was used as directed in the manufacturer's instructions. Also, unless otherwise indicated, other similar equipment can be used as well know to those skilled in the art.

Unless otherwise indicated, all equipment and reagents were used as directed in the manufacturer's instructions. Further, unless otherwise indicated, that suitable substitution for said equipment and reagents would be available and well know to those skilled in the art.

(1) RODOS dry powder disperser (Sympatec Inc., Princeton, N.J.)
(2) HELOS laser diffractometer (Sympatec Inc., N.J.)
(3) Single-stage Andersen impactor (Andersen Inst., Sunyrna, Ga.)
(4) AeroDisperser (TSI, Inc., Amherst, Mass.)
(5) Aerosizer (TSI Inc., Amherst, Mass.)
(6) blister pack machine, Fantasy Blister Machine (Schaefer Tech, Inc., Indianapolis, Ind.)
(7) collapsed Andersen cascade impactor (consisting of stage 0 as defined by manufacturer) and the filter stage (Anderson Inst., Sunyra, Ga.)
(8) a spirometer (Spirometrics, USA, Auburn, Me.)
(9) a multistage liquid impinger (MSLI) (Erweka, USA, Milford, Conn.)
(10) fluorescent spectroscope (Hitachi Instruments, San Jose, Calif.)
(11) gamma camera (generic)
Reagents
albuterol sulfate particles (Profarmco Inc., Italy)
human growth hormone (Eli Lilly, Indianapolis, Ind.)
size #2 methyl cellulose capsules (Shionogi, Japan)
blister packs (Heuck Foils, Well, N.J.)
DPPC (Avanti, Alabaster, Ala.)

As discussed in more detail in the Example section below, the methods of the instant invention require powders which exhibit good aerosolization properties from a simple inhaler device. In order to determine if a powder has the appropriate aerosolization properties, the powder is tested for deaggregation and emission properties. Although those skilled in the art will recognize equivalent means to measure these properties, an example of an in vitro test which demonstrates delivery of a mass of powder onto an impactor is performed. The powder to be tested is introduced into a powder dispensing apparatus, for example a RODOS dry powder disperser at varying shear forces. This is accomplished by manipulating the regulator pressure of the air stream used to break up the particles. The geometric size is measured to determine whether a powder has successfully deaggregated under the conditions. In addition to the deaggregation properties, it is possible to evaluate the ability of a powder to emit from a simple, breath-activated inhaler. Examples of inhalers suitable for the practice of the instant invention are the SPINHALER® (Fisons, Loughborough, U.K.), ROTAHALER® (Glaxo-Wellcome, Research Triangle Park (RTP), North Carolina), FLOWCAPS® (Hovione, Loures, Portugal), INHALATOR® (Boehringer-Ingelheim, Germany), and the AEROLIZER® (Novartis, Switzerland). It will be appreciated that other inhalers such as the Diskhaler (Glaxo-Wellcome, RTP, N.C.) may also be used. Especially suitable inhalers are the simple, dry powder inhalers (U.S. Pat. Nos. 4,995,385 and 4,069,819). A specific non-limiting example describing an experiment to determine the deaggregation and emission properties of three different powders is described in further detail herein. Briefly, three different dry powders believed to have different deaggregation properties were characterized. The first powder was micronized albuterol sulfate particles. The second and third powders were prepared by dissolving a combination of excipients and a bioactive agent in an ethanol/water solvent system and spray drying to create dry powders. The geometric diameter, tap density and aerodynamic diameter of the three powders were determined.

The Applicants introduced the powders into and dispersed the powder through an orifice in the RODOS dry powder disperser at varying shear forces by manipulating the regulator pressure of the air stream used to break up the particles. The Applicants obtained the geometric size distribution from the HELOS laser diffractometer as the powder exited and recorded the median value. The data was summarized and plotted as the mass median geometric diameter (MMGD) against pressure.

Applicants postulated and through experimentation disclosed herein found that at high pressure, for example 3 or 4 bars, all three powders exited the disperser as primary (deaggregated) particles. This supports the finding that relatively high energy successfully deaggregates all three powders.

However at pressures below 2 bars, which more closely corresponds with physiological breath rate, the micronized powder (Powder 1 Table 1) exited the orifice in an aggregated state, evidenced by a mean particle size leaving the orifice that was greater than the powder's primary particle size. This is not the case for the spray-dried powders (Powders 2 and 3, Table 1), which emitted from the orifice at approximately their primary particles size. These powders are highly dispersible powders.

To further evaluate the ability of the three powders to emit from a simple, breath-activated inhaler, Applicants placed 5 mg of each powder in a size #2 methyl cellulose capsule and inserted the capsule into a breath-activated inhaler. It will be appreciated by those skilled in the art that the receptacle into which the powders are placed will depend on the type of inhaler selected. The results are discussed in the Examples below. Generally, applicants found that given the relatively low energy supplied by the inhaler to break up the powder, the micronized albuterol sulfate powder was emitted from the inhaler as an aggregate with a geometric diameter greater than 30 microns, even though the primary particle size, as measured by RODOS, was on the order of 2 microns. On the other hand, the highly dispersible particles of spray-dried albuterol sulfate or hGH were emitted at particle sizes that were very comparable to their primary particle size. The same results were obtained from measurements of the aerodynamic diameter, with spray-dried particles emitting with very similar aerodynamic diameters as compared to the primary particles. Using the methods of the instant invention, one skilled in the art can achieve high-efficiency delivery from a simple breath-activated device by loading it with powder that is highly dispersible.

A further feature of the instant invention is the ability to emit large percentages of a nominal dose at low energy not only from a single-dose, breath-actuated inhaler but also from a range of breath-actuated Dry Powder Inhalers (DPIs).

To illustrate that a highly dispersible powder can efficiently emit and penetrate into the lungs from a range of breath-activated DPIs, Applicants prepared a spray-dried powder comprised of sodium citrate, DPPC, calcium chloride buffer, and a rhodamine fluorescent label. This is explained thoroughly in Example 2. The powder possessed a median aerodynamic diameter of 2.1 µm (measured by the AeroDisperser and Aerosizer) and a geometric diameter of 11.0 µm (measured using the RODOS/HELOS combination described above). Applicants found that the powders tested displayed excellent deaggregation properties.

In particular, Applicants placed 5 mg of the powders to be tested in the capsules using a semi-automated capsule filling device in the following inhalers: a breath-activated inhaler under development by the applicant, the SPINHALER® (Fisons, Loughborough, U.K.), ROTAHALER® (Glaxo-Wellcome, RTP, NC), FLOWCAPS®(Hovione, Loures, Portugal), INHALATOR® (Boehringer-Ingelheim, Germany) and the AEROLIZER® (Novartis, Switzerland). We also tested the Diskhaler (Glaxo-Wellcome, RTP, NC), for which 3 mg of the powder was machine-filled into the blister packs. Applicants connected each inhaler to a collapsed Andersen cascade impactor (consisting of stage 0 and the filter stage) and extracted air at 60 L/minute for 2 seconds after actuating the device. The fine particle fraction less than stage 0, having a 4.0 µm cut-off, was determined using fluorescent spectroscopy.

Applicants found that in each case, approximately 50% or more of the emitted dose displayed a mean aerodynamic diameter (Da) less than 4 µm in size, indicating that the powder efficiently entered the lungs of a human subject at a physiological breath rate, despite the simplicity of these breath-activated devices.

Figure 7:
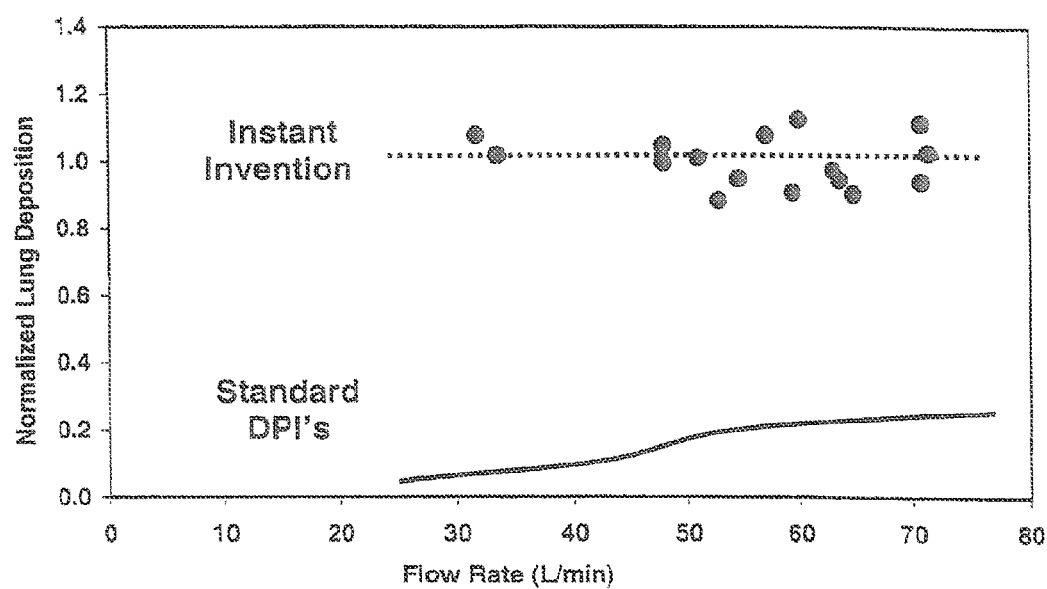

In order to test the highly dispersible powders in vivo, Applicants performed human deposition studies, as described in Example 3, to determine whether a highly dispersible powder emitted from a simple breath-actuated inhaler could produce highly efficient delivery to the lungs (>50% of the nominal dose). This is especially important because many devices rely on inhalation by the patient to provide the power to break up the dry material into a free-flowing powder. Such devices prove ineffective for those lacking the capacity to strongly inhale, such as young patients, old patients, infirm patients or patients with asthma or other breathing difficulties. An advantage of the method of the instant invention is that highly efficient delivery can be achieved independent of the flow rate. Thus, using the methods of the invention, even a weak inhalation is sufficient to deliver the desired dose. This is surprising in light of the expected capabilities of standard DPIs. As can be seen in FIG. 7, using the methods described herein, superior delivery can be achieved at flow rates ranging from about 25 L/min to about 75 L/min, as compared to standard DPIs. The methods of the instant invention can be optimized at flow rates of at least about 20 L/min to about 90 L/min.

Figure 5:
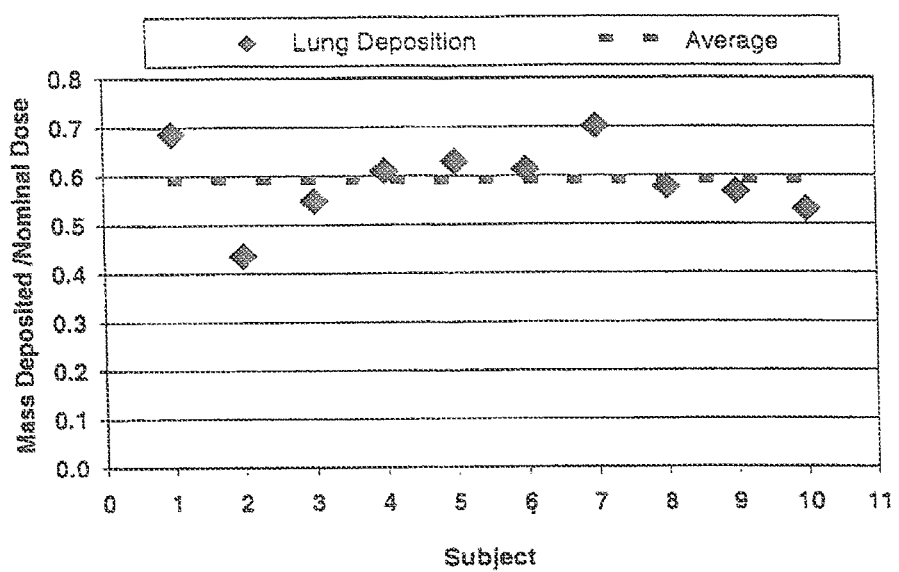

Powder possessing the following characteristics: Dg=6.7 µm; p=0.06 g/cc; and Da=1.6 µm was labeled with $^{99m}$Tc nanoparticles. Equivalence between the mass and gamma radiation particle size distributions was obtained and is discussed in detail in Example 3 below. Approximately 5 mg of powder was loaded into size 2 capsules. The capsules were placed into a breath-activated inhaler and actuated. Ten healthy subjects inhaled through the inhaler at an approximately inspiratory flow rate of 60 L/min. as measured by a spirometer. The deposition image was obtained using a gamma camera. The percentage of lung deposition (relative to the nominal dose) obtained from the ten subjects is shown in FIG. 5. The average lung deposition, relative to the nominal dose, was 59.0%. Those skilled in the art will recognize that such deposition levels confirm that a highly dispersible drug powder can be inhaled into the lungs with high efficiency using a single breath-actuated inhaler.

Further, Applicants have discovered that the same preparations of a highly dispersible powder that had excellent aerosolization from a single inhaler can be used to deliver a surprisingly high dose in a single inhalation. The highly dispersible powder can be loaded into a large pre-metered dose (50 mg) or a smaller pre-metered dose (6 mg). The particle characteristics of the powder were as follows: Dg=10.6 µm; p=0.11 g/cc; Da=3.5 µm. One skilled in the art would appreciate the possible ranges of characteristics of particles suitable for use in the instant invention, as disclosed previously herein.

The aerodynamic particle size distributions were characterized using a multistage liquid impinger (MSLI) operated at 60 L/min. Size 2 capsules were used for the 6 mg dose and size 000 capsules were used for the 50 mg dose. Applicants compared the two particle size distributions obtained for the 6 and 50 mg doses. The fine particle fraction <6.8 µm (relative to the total dose ($FPF_{TD}$<6.8 µm)) for the 6 and 50 mg doses was 74.4% and 75.0%, respectively. Thus, Applicants have demonstrated that a large dose of drug can be delivered to the lungs as efficiently as a small drug dose by combining the properties of a highly dispersible powder.

EXAMPLES AND TABLES

Exemplification

Unless otherwise noted, the apparatus and reagents used have been obtained from the sources previously listed herein.

Example 1

The powders suitable for use in the methods of the instant invention are required to possess properties which exhibit good aerosolization from a simple inhaler device. To determine the properties, Applicants characterized three different dry powders believed to have different deaggregation properties. The first powder to be tested was submicron albuterol sulfate particles obtained from Spectrum Labs (Laguna Hills, Calif.). The second and third powders were prepared by dissolving a combination of excipients and a bioactive agent in an ethanol/water solvent system and spray-drying the mixture.

Preparation of Microparticles:

Placebo particle composition was 70/20/10% DPPC/sodium citrate/calcium chloride. 0.2 grams of sodium citrate and 0.1 grams of calcium chloride were dissolved in 0.11 liters of water. A DPPC solution in ethanol was prepared by dissolving 0.7 g DPPC (DL-α-phosphatidylcholine dipalmitoyl, Avanti Polar Lipids, Alabaster, Ala.) in 0.89 liters of 95% ethanol. The sodium citrate/calcium chloride solution and the DPPC/ethanol solution were then mixed together. The final total solute concentration was 1.0 g/L, made up of 0.70 g/L DPPC, 0.2 g/L sodium citrate and 0.1 g/L calcium chloride in 85% ethanol/15% water.

hGH (human growth hormone) particle composition was: 58/38.5/3.5 hGH/DPPC/Sodium Phosphate. 1.16 grams of hGH (Lilly, Indianapolis, Ind.) was dissolved in 300 mL of sodium phosphate buffer (10 mM, pH 7.4). 0.77 grams of DPPC was dissolved in 700 mL of ethanol. The two solutions were then combined, resulting in a final solute concentration of 2 g/L in 70%/30% ethanol/water.

Albuterol sulfate particle composition was 76/20/4 DSPC/Leucine/Albuterol Sulfate. 2.28 grams of DSPC (disteoroyl phosphatidylcholine, Avanti Polar Labs) and 0.6 grams of Leucine (Spectrum Labs, Laguna Hills, Calif.) were dissolved in 700 mL of ethanol. 0.12 grams of albuterol sulfate (Profarmco, Italy) was dissolved in 300 mL of water and then the two solutions were combined to yield a final solute concentration of 3 g/L in 70%/30% ethanol/water.

Spray Drying:

A Nitro Atomizer Portable Spray Dryer (Niro, Inc., Columbus, Md.) was used to produce the dry powders. Compressed air with variable pressure (1 to 5 bar) ran a rotary atomizer (2,000 to 30,000 rpm) located above the dryer. Liquid feed with varying rates (20 to 66 mL/min) was pumped continuously by an electronic metering pump (LMI, model #A151-192s, Acton, Mass.) to the atomizer Both the inlet and outlet temperatures were measured. The inlet temperature was controlled manually; it could be varied between 100° C. and 400° C. and was established at 100, 110, 150, 175, or 200° C., with a limit of control of 5° C. The outlet temperature was determined by the inlet temperature and such factors as the gas and liquid feed rates: it varied between 50° C. and 130° C. A container was tightly attached to the cyclone for collecting the powder product.

Results

The geometric diameter and tap density of the three powders are shown in Table 1.

TABLE 1

| Powder | Dg (μm) | ρ(g/cc) |
|---|---|---|
| Micronized Alb. Sulfate (1) | 2.5 | 0.26 |
| Spray-Dried Alb. Sulfate (2) | 8.0 | 0.20 |
| Spray-Dried hGH (3) | 14.5 | 0.07 |

To evaluate the deagglomeration properties of the three powders, Applicants introduced the powders into a RODOS dry powder disperser and varied the shear force in order to break up the particles by manipulating the regulator pressure of the air stream. Subsequently, following the manufacturer's instructions, Applicants obtained the geometric size distribution from the HELOS laser diffractometer and recorded the median value. The data was summarized and plotted as volume median geometric diameter (MMGD) against pressure.

FIG. 1 shows the results of this experiment. Applicants have demonstrated that at high pressure, about greater than 2 bars and especially about 3 to 4 bars, all three powders exit the disperser as primary (deaggregated) particles. This supports the finding that at relatively high energy, the three powders were deaggregated. However at pressures below 2 bars, the micronized powder (Powder 1) exited the orifice in an aggregated state. Evidence of this can be seen by a mean particle size leaving the orifice that was greater than the powder's primary particle size. This was not the case for the spray-dried powders (Powders 2 and 3), which emitted from the orifice at approximately their primary particle size. Powders 2 and 3 were highly dispersible powders.

Particles of the present invention were further characterized by the following techniques. The primary geometric diameter was measured using a RODOS dry powder disperser (Sympatec, Princeton, N.J.) in conjunction with a HELOS laser diffractometer (Sympatec). Powder was introduced into the RODOS inlet and aerosolized by shear forces generated by a compressed air stream regulated at 4 bar. The aerosol cloud was subsequently drawn into the measuring zone of the HELOS, where it scattered light from a laser beam and produced a Fraunhofer diffraction pattern used to infer the particle size distribution.

The geometric diameter emitted from the breath-activated inhaler was measured using an IHA accessory (Sympatec) with the HELOS laser diffractometer. The IHA adapter positions the DPI in front of the measuring zone and allows air to be pulled through the DPI which aerosolizes the powder. Vacuum was drawn at 30 L/min to disperse powder from the AIR inhaler and the geometric diameter was measured by Fraunhofer diffraction.

The primary aerodynamic diameter was measured using an AeroDisperser/Aerosizer (TSI Inc., Amherst, Mass.). The sample powder was aerosolized by an inlet air stream at 1 psi in the AeroDisperser and then accelerated to sonic velocity into the Aerosizer. The Aerosizer measures the time taken for each particle to pass between two fixed laser beams, which is dependent on the particle's inertia. The TOF (time of flight) measurements were subsequently converted into aerodynamic diameters using Stokes law.

The emitted aerodynamic diameter from the AIR inhaler was determined using the AeroBreather (TSI Inc., Amherst, Mass.) in conjunction with the Aerosizer (TSI, Inc.). The powder was aerosolized from the inhaler at 30 L/min into the AeroBreather chamber and allowed to settle into the Aerosizer.

Figure 2A:
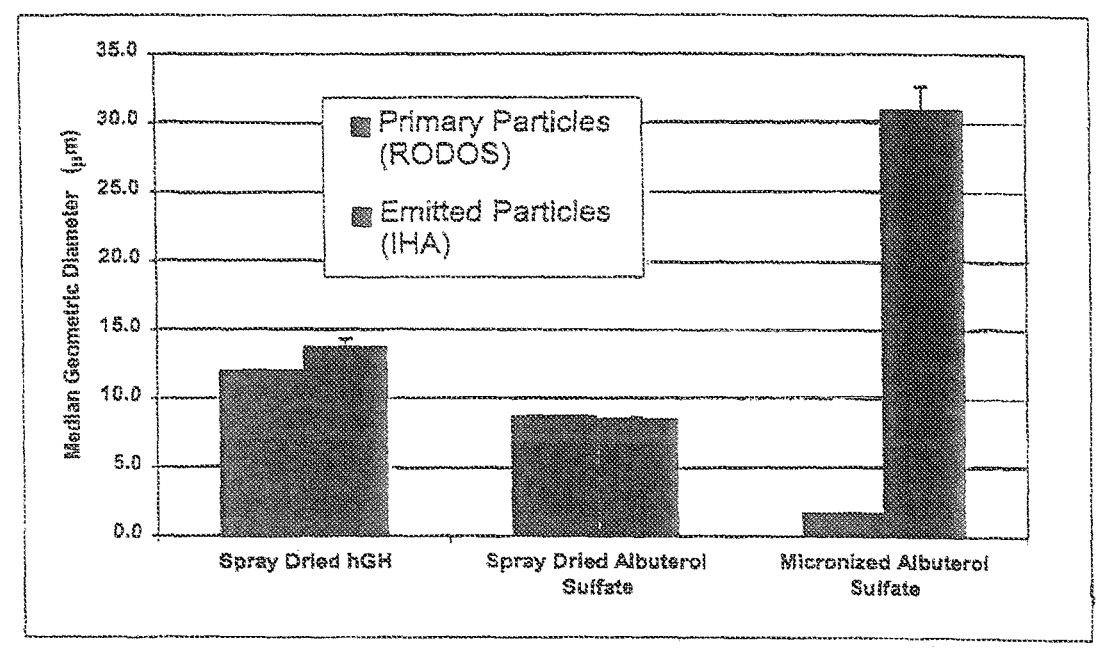
Figure 2B:
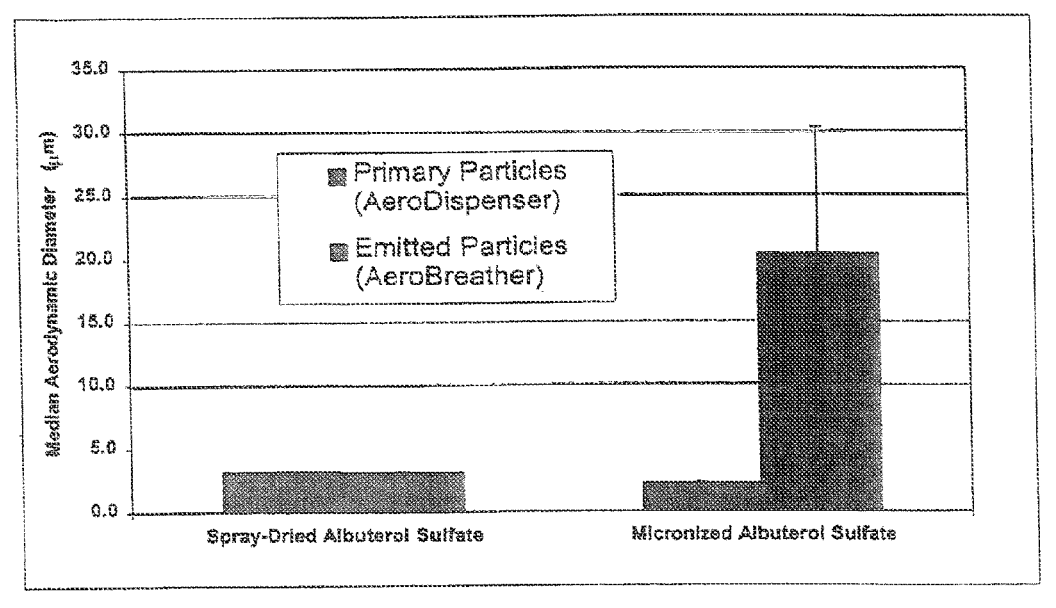

Using these techniques, Applicants compared the primary size from the dry powder disperser at 4 bar to the emitted size from the AIR inhaler at 30 L/min (FIG. 2A). As can be seen, the spray-dried hGH-(Powder 2) and spray-dried albuterol sulfate-(Powder 3) emitted particle size was almost identical to their measured primary particle size, which was not the case for the micronized albuterol sulfate (Powder 1). In addition, Applicants measured primary and emitted aerodynamic size for the spray-dried albuterol sulfate and compared it to the micronized albuterol sulfate (FIG. 2B). Again, the spray-dried albuterol sulfate emitted with a nearly identical aerodynamic diameter as its primary particle's aerodynamic diameter while the micronized albuterol sulfate emitted with a much larger aerodynamic diameter than its primary particle's aerodynamic diameter. This further confirms that the spray-dried powders of the present invention disperse into respirable particles while the micronized drug remains nonrespirable even though its primary size is respirable.

The results of this example demonstrate that using the methods of the instant invention, Applicants achieved high-efficiency delivery from a simple breath-activated device by loading it with powder that is highly dispersible.

Example 2

To illustrate that a highly dispersing powder can efficiently emit and penetrate into the lungs from a range of breath-activated dry powder inhalers (DPIs), Applicants prepared a spray-dried powder comprised of sodium citrate, DPPC, calcium chloride buffer and a trace amount of a rhodamine fluorescent label. The powder possessed a median aerodynamic diameter of 2.1 μm (measured by the AeroDisperser and Aerosizer) and a geometric diameter of 11.0 μm (measured using the RODOS dry powder disperser and HELOS laser diffractometer, as described herein) and displayed excellent deaggregation properties similar to the spray-dried powders in Example 1.

Applicants placed 5 mg of the powder in the capsules using a semi-automated capsule filling device in the following inhalers: a breath-activated inhaler under development by Applicants (AIR™ Inhaler), the SPINHALER® (Fisons, Loughborough, U.K.), ROTAHALER® (Glaxo-Wellcome, RTP, NC), FLOWCAPS® (Hovione, Loures, Portugal), INHALATOR® (Boehringer-Ingelheim, Germany), and the AEROLIZER® (Novartis, Switzerland). Applicants also tested the Diskhaler (Glaxo-Wellcome, RTP, NC), for which 3 mg of the powder was machine-filled into the blister packs. Applicants connected each inhaler to a collapsed Andersen cascade impactor (consisting of stage 0 and the filter stage) and extracted air at 60 L/minutes for 2 seconds after actuating the device. The fine particle fraction less than stage 0, having a 4.0 μm cut-off, was determined using fluorescent spectroscopy.

Figure 3:
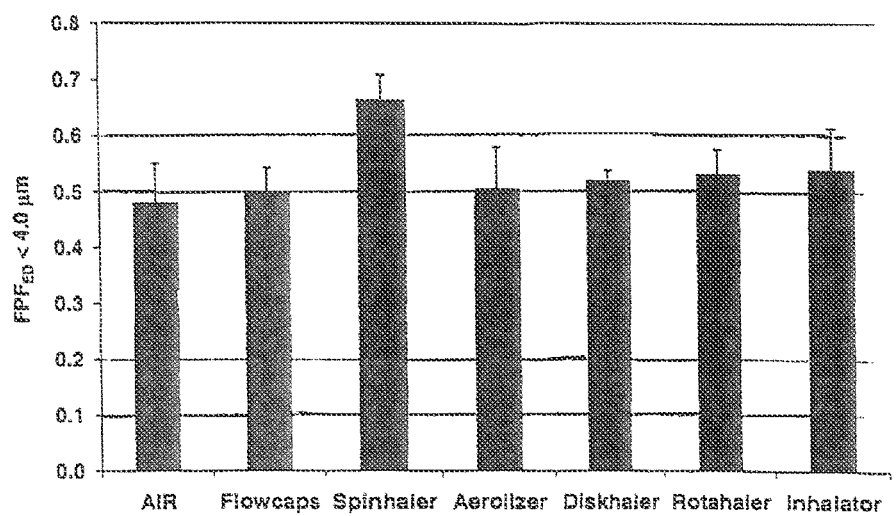

FIG. 3 shows the results from the study. Applicants found that in each case, approximately 50% or more of the emitted dose displayed a mean aerodynamic diameter (Da) less than 4 μm in size, indicating that the powder would efficiently enter the lungs of a human subject at a physiological breath rate, despite the simplicity of these breath-activated devices. Applicants also demonstrated that using the methods of the instant invention, large percentages of a nominal dose at low energy were emitted from not only single dose, breath-actuated inhalers but also from a range of breath-actuated dry powder inhalers (DPIs).

Example 3

A human deposition study was performed to determine whether a highly dispersible powder emitted from a simple breath-actuated inhaler could produce highly efficient delivery to the lungs (>50% of the nominal dose). Powders possessing the following characteristics were used: Dg=6.7 μm; ρ=0.06 g/cc; Da=1.6 μm.

The powder was labeled with $^{99m}$Tc (Technetium) nanoparticles.

Human Deposition Studies

Gamma scintigraphy is an established methodology for assessing the pattern of deposition of inhaled particles. In this example the test substance is labelled with a small dose of the radioisotope $^{99m}$Tc at the InAMed laboratories (Gauting, Germany). Determination of the lung border is enhanced by undertaking an $^{81m}$Kr (Krypton) ventilation scan. Inspiratory flow rates were monitored to ensure that a deep, comfortable inhalation was performed during the deposition study. The range of peak inspiratory flow rates (PIFR) for a deep comfortable inhalation through the breath-activated inhaler was assessed prior to the start of the study. PIFRs outside of the specified range were repeated.

Studies were performed using 10 normal subjects. A baseline ventilation scan was undertaken to assist in defining the lung borders. Lung function was assessed before and after each inhalation test. Deposition was determined following inhalation using gamma scintigraphy. Inspiratory flow rates through a breath-activated inhaler were monitored during the deposition using a spirometer.

Subjects were trained to inhale through a breath-activated inhaler with a deep, comfortable inhalation. Subjects were further trained to achieve a peak inspiratory flow rate (PIFR) through a breath-activated inhaler within a specified range which represented a deep, comfortable inhalation. The breath-activated inhaler was actuated and attached to the spirometer to monitor the inspiratory flow rate during the deposition study. The subject removed a capsule from the appropriate box, according to the predetermined randomization schedule, and placed it in the inhaler/spirometer device immediately prior to use.

Each subject was relaxed and breathing normally (for at least 5 breaths) prior to placing the inhaler mouthpiece in his/her mouth at the end of a normal exhalation. The subject inhaled through the mouth with a deep, comfortable inhalation until the lungs were full. The subject then held his/her breath for approximately 5 seconds (by counting slowly to 5). Deposition was measured using a gamma camera immediately after exhalation. A further lung function test was then performed using a Jaeger body plethysmograph, (Jaeger, Würzburg, Germany).

Materials and Methods

The placebo powder, comprised of 70/20/10% by weight DPPC/Sodium Citrate/Calcium Chloride, that was used had the following characteristics: Dg=6.7 um; __=0.06 g/cc; Da=1.6 um. The primary aerodynamic particle size characteristics were obtained using time-of-flight (AeroSizer/AeroDisperser) and the geometric particle size characteristics were obtained using laser diffraction (measured using the RODOS dry powder disperser and HELOS laser diffractometer, as described herein) operated at 1 and 2 bar. Emitted aerodynamic particle size characteristics were obtained using Andersen cascade impaction (gravimetric analysis) operated at 28.3 L/min, for a total air volume of 2 L. Geometric particle size characteristics were obtained using laser diffraction (IHA/HELOS, Sympatec, N.J.) operated at 60 L/min.

Powder Radiolabeling

Placebo powder was filled in a reservoir which was closed by an 0.2 μm filter. A $^{99m}$Tc solution (0.5 mL $^{99m}$Tc in isotonic saline added to 100 mL of deionized water) was filled in a Pari Jet nebulizer which was placed in a drying chamber. The Pari Jet nebulizer was activated for 3 min to nebulize 1.5 ml of the $^{99m}$Tc solution. The $^{99m}$Tc particles were dried in this chamber and led through the reservoir containing the powder. The humidity in the labeling chamber was controlled and never exceeded 30% relative humidity.

Because of the short half life of the $^{99m}$Tc, the labeling was performed 2 to 4 hours before the inhalation. The activity of the powder was corrected for the physical decay of the Technetium, in order to determine the actual activity which was available at the beginning of the inhalation.

The emitted aerodynamic particle size distribution of the post-labeled powder was obtained using an 8-stage Andersen cascade impactor (gravimetric analysis) to verify that the radiolabeling process did not affected the particle size distribution.

Size 2 capsules were hand filled with 5(±1) mg of the radiolabeled powder. Each capsule was numbered and its filled weight and level of radioactivity were recorded. The subject took a capsule and placed it in the inhaler/spirometer device immediately prior to use.

Methodology for the Determination of Powder in the Regions of the Lung

The inhalation of the labeled porous particles was performed while the subject was sitting with his back against the gamma camera. After inhalation a gamma scintigraphic image was taken while the subject was sitting upright with his/her back in front of the camera. The inhalation time and breath holding period was recorded. The size of the lungs was determined by an $^{81}$Kr scan. This radioactive gas was inhaled by the subject before or at the end of the study.

From the Krypton ventilation scan of the subject, the outline of the lungs was determined. Because the subject was sitting in the same position during the Krypton scan and the powder inhalation test study, there were 4 regions of interest (ROI) that were defined: left lung, right lung, stomach and oropharynx (including upper part of trachea).

These 4 ROIs were copied to the gamma camera image of the powder inhalation. In a region outside of the subject's lung, the background activity was defined and subtracted pixel by pixel from the entire image. The number of counts was then determined for each of the 4 ROIs. These numbers were corrected by an attenuation factor for the single regions. After this correction, the relative amounts of intrathoracic particle deposition and extrathoracic particle deposition was determined.

Figure 4:
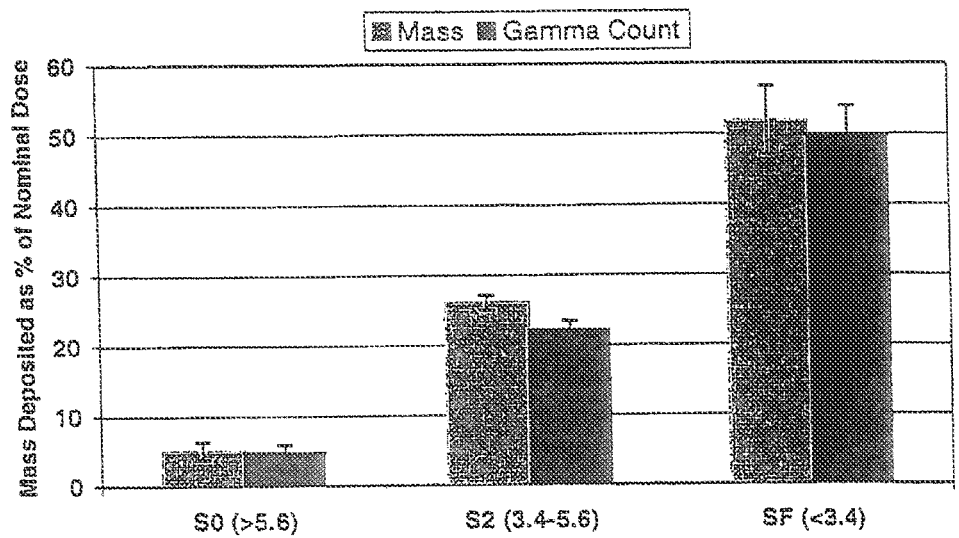

Equivalence between the mass and gamma radiation particle size distributions was obtained, as shown in FIG. 4. Approximately 5 mg of powder was loaded into size 2 capsules. The capsules were placed into a breath-activated inhaler under development by the applicant (AIR inhaler) and actuated. Ten healthy subjects inhaled through the inhaler at an approximate inspiratory flow rate of 60 L/min (the actual inspiratory flow rate varied from subject to subject over a range of 20 to 90 L/min., consistent with the normal range of inspiratory flow rates in humans). 60 L/min is a good average flow rate and is what is used experimentally to mimic inspiratory flow. As measured by a spirometer, the deposition image was obtained using a gamma camera. The percentage of lung deposition (relative to the nominal dose) obtained from the ten subjects is shown in FIG. 5. The average lung deposition relative to the nominal dose was 59.0%.

Through this experiment, the Applicants confirmed that highly dispersible powder comprising drug can be inhaled into the lungs with high efficiency using a simple breath-actuated inhaler.

Example 4

To demonstrate that the same preparations of a highly dispersing powder that had excellent aerosolization properties from a simple inhaler can be used to deliver a surprisingly high dose in a single inhalation, Applicants prepared a highly dispersible powder and loaded the powder to obtain either a large pre-metered dose (50 mg) or a smaller pre-metered dose (6 mg). The particle size characteristics of the powder were as follows: Dg=10.6 µm; ρ=0.11 g/cc; Da=3.5 µm.

Figure 6:
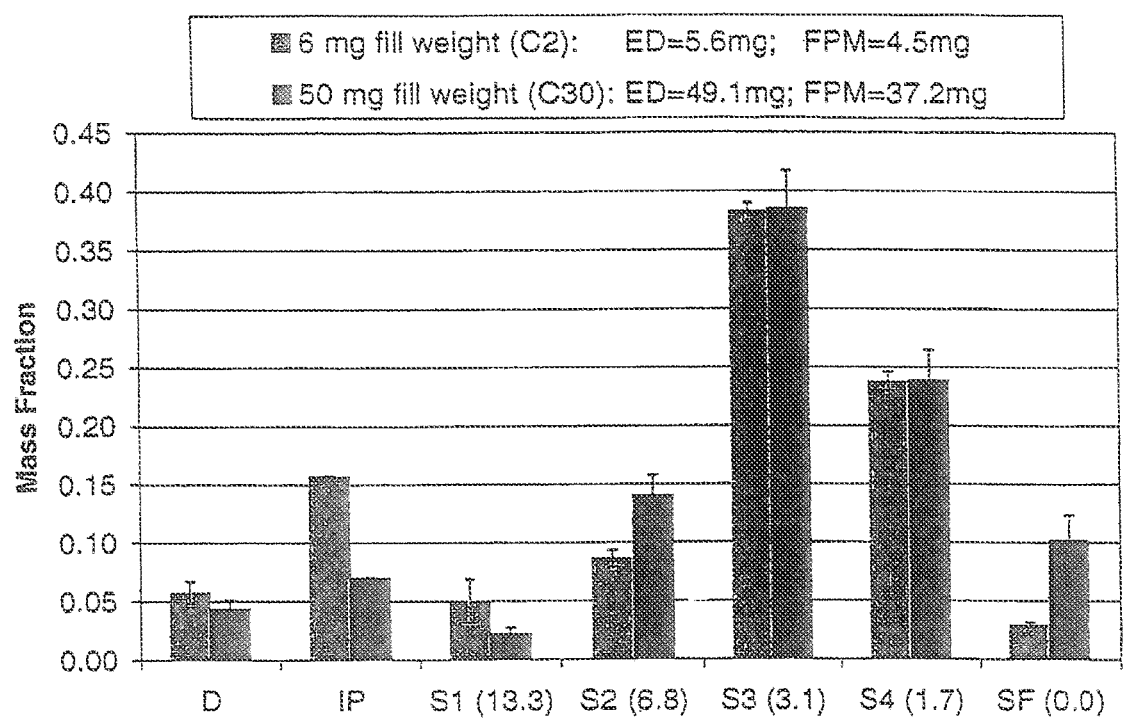

The aerodynamic particle size distributions were characterized using a multistage liquid impinger (MSLI) operated at 60 L/min. Size 2 capsules were used for the 6 mg dose and size 000 capsules were used for the 50 mg dose. FIG. 6 shows the results comparing the two particle size distributions obtained for the 6 and 50 mg doses. The fine particle fraction <6.8 µm relative to the total dose (FPF$_{TD}$<6.8 µm) for the 6 and 50 mg doses were 74.4% and 75.0%, respectively.

This experiment demonstrated that a surprisingly large dose of drug can be delivered to the lungs with equal efficiency as a small drug dose by combining the properties of a highly dispersible powder with the methods of the instant invention.

Example 5

Particles comprising L-Dopa and suitable for inhalation were produced as follows: 2.00123 g DPPC (Avanti Polar Lipids, Lot #G160PC-25) was added to 2.80 L of ethanol and stirred to dissolve. 0.0817 g L-Dopa (Spectrum, Lot 0Q0128, Laguna Hills, Calif.), 0.9135 g Sodium Citrate (Dehydrate) (Spectrum Lot NX0195), and 0.5283 g Calcium Chloride (Dehydrate) (Spectrum Lot NT0183) were added to 1.2 L of water and dissolved. The solutions were combined by adding the water solution to the ethanol solution and then the solutions were allowed to stir until the solution was clear. The weight percent of the formulation was approximately: 20% L-Dopa, 50% DPPC, 20% Sodium Citrate, 10% Calcium Chloride.

The final solution was then spray-dried in a Niro dryer (Niro, Inc., Columbus, Md.) using a rotary atomizer and nitrogen drying gas following the direction of the manufacturer, using the following spray conditions: T$_{inlet}$=120 C, T$_{outlet}$=54 C, Feed Rate=65 ml/min, Heat Nitrogen=38 mm H20, Atomizer Speed=20,000 rpm (V24 atomizer used).

The resulting particle characteristics were: Mass Median Aerodynamic Diameter (MMAD)=2.141 Mm and Volume Median Geometric Diameter (VMGD)=10.51 Mm.

Under ketamine anesthesia, six rats received pulmonary administration of the formulation described above (20/50/20/10 L-Dopa/DPPC/Sodium Citrate/Calcium Chloride).

Figure 8:
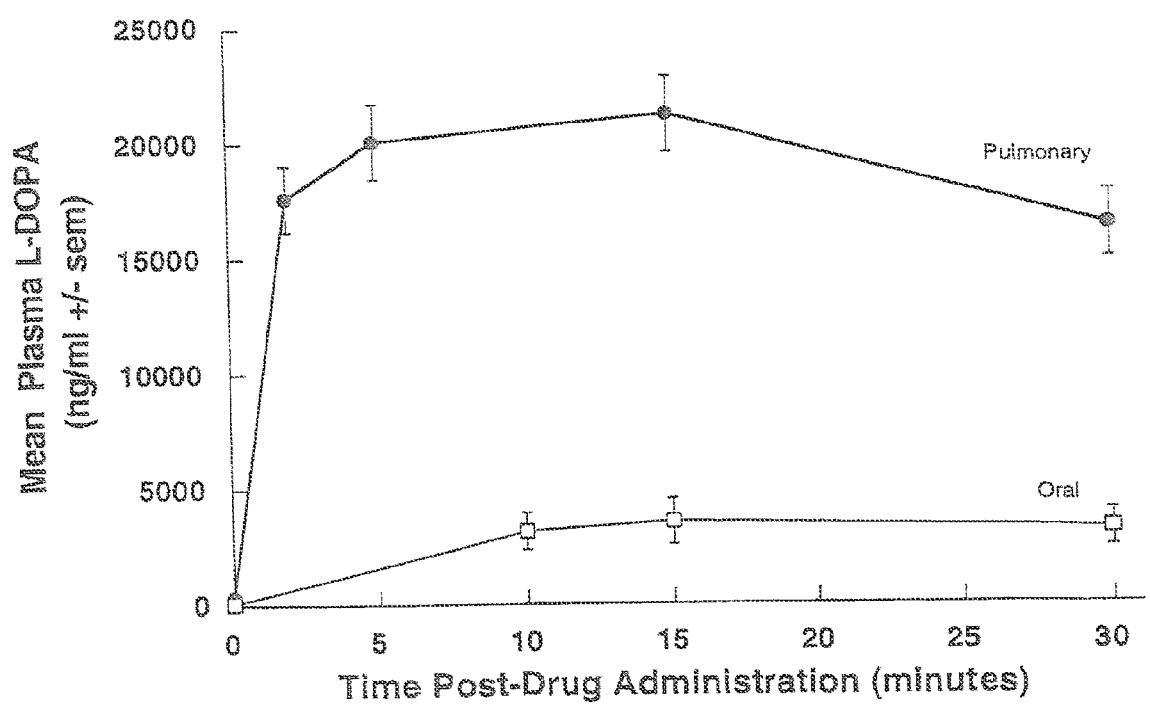

The results are shown in FIG. 8. This figure shows blood levels of L-Dopa following administration via oral gavage or direct administration into the lungs via insufflation. L-Dopa levels were measured using both HPLC. Animals received an IP injection of the peripheral decarboxylase inhibitor carbidopa (200 mg/kg) 1 hour prior to administration of L-Dopa. Under ketamine anesthesia, the animals were divided into 2 groups. In the first group, animals were fasted overnight and L-Dopa (8 mg) was suspended in saline contained 1% methylcellulose and given via oral gavage. In the second group, insufflation was used to delivery the L-Dopa formulation directly into the lungs. Blood samples (200 Ml) were withdrawn from a previously placed femoral cannula at the following time points: 0 (immediately prior to L-Dopa administration), 2, 5, 15, and 30 minutes following L-Dopa administration. The increase in blood levels of L-Dopa over time following oral administration was modest. In contrast, administration into the lungs produced a robust and rapid rise in L-Dopa levels. L-Dopa levels in this group remained elevated relative to oral delivery at 30 minutes post drug administration. Data were normalized to a dose of 8 mg/kg (the total oral gavage dose). Data are presented as the mean±SEM ng 1-Dopa levels/ml blood.

Example 6

Ketoprofen/DPPC/maltodextrin particles were prepared and administered in vivo.

Ketoprofen (99.5%) was obtained from Sigma, (St. Louis, Mo.), dipalmitoyl phosphatidyl choline (DPPC) from Avanti Polar Lipids, (Alabaster, Ala.) and maltodextrin,M100 (Grain Processing Corp., Muscatine, Iowa).

To prepare ketoprofin/DPPC/Maltodextrin solutions, maltodextrin (0.598 g) was added to 0.60 L USP water. DPPC (0.901 g) was added to 1.40 L ethanol and stirred until dissolved. The water and ethanol solutions were combined, resulting in a cloudy solution. 500 ml of this stock solution was used for each run. The addition of ketoprofen to the DPPC/Maltodextrin stock solution is described in Table 2.

A Niro Atomizer Portable Spray Dryer (Niro, Inc., Columbus, Md.) was used to produce the dry powders. Compressed air with variable pressure (1 to 5 bar) ran a rotary atomizer (2,000 to 30,000 rpm) located above the dryer. Liquid feed of the ketoprofin/DPPC/Maltodextrin solutions, with varying rate (20 to 66 ml/min), was pumped continuously by an electronic metering pump (LMI, model #A151-192s) to the atomizer. Both the inlet and outlet temperatures were measured. The inlet temperature was controlled manually; it could be varied between 100° C. and 400° C., with a limit of control of 5° C. The outlet temperature was determined by the inlet temperature and such factors as the gas and liquid feed rates: it varied between 50° C. and 130° C. A container was tightly attached to the 6" cyclone for collecting the powder product. The spraying conditions for each solution is given in Table 3, which shows that the spraying conditions were held nearly constant throughout the study. The total recovery and yield for each solution is given in Table 4.

The particles were characterized using the Aerosizer (TSI, Inc., Amherst, Mass.) and the RODOS dry powder dispenser (Sympatec Inc., Princeton, N.J.) as instructed by the manufacturer. For the RODOS, the geometric diameter was measured at 2 bars. The material from run #5 was also characterized using a gravimetric collapsed Andersen Cascade Impactor (ACI, 2 stage, Anderson Inst., Sunyra, Ga.). The samples were examined using a scanning electron microscope (SEM).

Table 4 indicates that increasing the weight % of ketoprofen led to a decrease in yield. The addition of ketoprofen to the stock solution linearly decreased yield. This may be due to a decrease in melting temperature for DPPC when mixed with ketoprofen, leading to the yield loss.

Table 5 shows that the particles ranged in diameter from 8.8 to 10.2 mm (VMGD) and from 2.65 to 3.11 (MMAD). The lowest MMAD particles were for the 8.4% loading material (run #5).

Table 6 shows the results of a Andersen Collapsed Impactor study (ACI, gravimetric, n=2) of the material from run #5, the 8.4% loading material. The FPF below 5.6 µm and below 3.4 µm are consistent with respirable powders which are reasonably respirable.

TABLE 2

| Sample ID | Ketoprofen added (mg) | Total solids (g/L) | % Ketoprofen |
|---|---|---|---|
| Run #1 | 0 | 1.000 | 0 |
| Run #2 | 8.0 | 1.016 | 1.6 |
| Run #3 | 15.1 | 1.030 | 3.0 |
| Run #4 | 30.1 | 1.060 | 5.7 |
| Run #5 | 46.0 | 1.092 | 8.4 |
| Run #6 | 63.0 | 1.126 | 11.2 |

TABLE 3

| Sample ID | Temperature(° C.) Inlet | Temperature(° C.) Outlet | Liquid Feed (ml/min) | Gas Pressure (mmH$_2$O) | Rotor Speed (RPM) | Inlet Dewpoint (° C.) |
|---|---|---|---|---|---|---|
| Run #1 | 115 | 36 | 75 | 40 | 18,600 | −27.0 |
| Run #2 | 113 | 38 | 85 | 40 | 18,400 | −26.8 |
| Run #3 | 110 | 38 | 85 | 39 | 18,300 | −26.4 |
| Run #4 | 110 | 39 | 85 | 38 | 18,400 | −25.9 |
| Run #5 | 110 | 38 | 86 | 39 | 18,400 | −25.4 |
| Run #6 | 110 | 38 | 85 | 38 | 18,400 | −25.0 |

TABLE 4

| Sample ID | Weight Collected (mg) | Theoretical Yield (mg) | Actual Yield (% Theoretical) |
|---|---|---|---|
| Run #1 | 186 | 500 | 37.2 |
| Run #2 | 195 | 508 | 38.4 |
| Run #3 | 147 | 515 | 28.5 |
| Run #4 | 127 | 530 | 24.0 |
| Run #5 | 89 | 546 | 16.3 |
| Run #6 | 67 | 563 | 11.9 |

TABLE 5

| Sample ID | MMAD (µm) | Std Dev | VMGD (µm, 2 bar) |
|---|---|---|---|
| Run #1 | 3.11 | 1.48 | 9.0 |
| Run #2 | 3.01 | 1.37 | 9.3 |
| Run #3 | 2.83 | 1.40 | 10.3 |
| Run #4 | 2.84 | 1.41 | 10.4 |
| Run #5 | 2.65 | 1.39 | 9.8 |
| Run #6 | 2.83 | 1.38 | 8.8 |

TABLE 6

| | |
|---|---|
| Stage 0 | 1.33 mg |
| Stage 2 | 2.75 mg |
| Stage F | 3.17 mg |
| Capsule Fill | 12.37 mg |
| Weight <5.6 µm | 5.92 |
| FPF$_{5.6}$ | 0.479 |
| Weight <3.4 µm | 3.17 |
| FPF$_{3.4}$ | 0.256 |

350 mg of 8% ketoprofen in 60/40 DPPC/maltodextrin were produced as described above and administered to 20 Sprague Dawley rats. Each of 8 rats were given 7 mg of powder via insufflation, and each of 7 rats were given 7 mg of powder dissolved in 50% ethanol orally. Time points were set at 0, 5, 15, 30, 60, 120, 240, 360 and 480 minutes. For t=0, 4 animals were tested without dosing. For each time point after, samples were taken from either 3 or 4 rats. Each rat was used for 4 time points, with 3 or 4 animals each in four groups. The animals were distributed as follows: 3 animals oral 5, 30, 120, 360; 4 animals insufflation 15, 60, 240, 480. Sufficient blood was drawn at each time point for the ketoprofen plasma assay.

Blood samples were centrifuged, the plasma collected and then frozen at −20° C. prior to shipment to the contract laboratory for analysis. The assay used in this study has a lower detection limit of 1.0 mg/ml. Rats were dosed with ketoprofen via either oral or pulmonary administration to determine if the pulmonary route would alter the time required to achieve maximum plasma concentration. The results show that the pulmonary delivery route leads to a very rapid uptake with occurring at ≤10 minutes. The rats that received oral doses of ketoprofen displayed somewhat anomalous pharmacokinetic behavior, with the relative bioavailability being about half of that displayed for rats dosed via the pulmonary route. This result was unexpected as ketoprofen is 90% orally bioavailable in the human model. This anomaly for the orally dosed rats does not, however, invalidate the significance of the early seen for the rats dosed via the pulmonary route.

Figure 9:
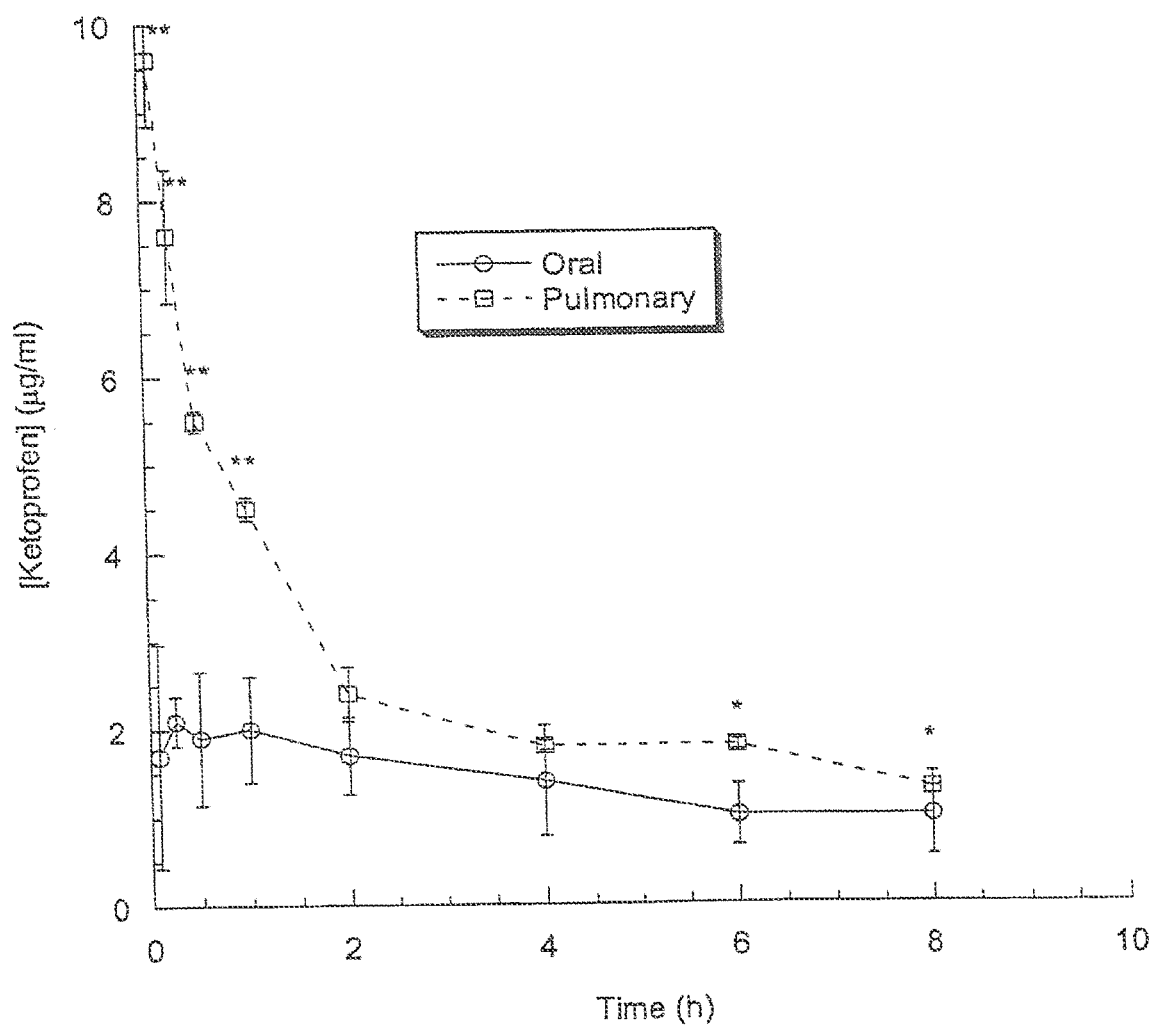
Figure 10:
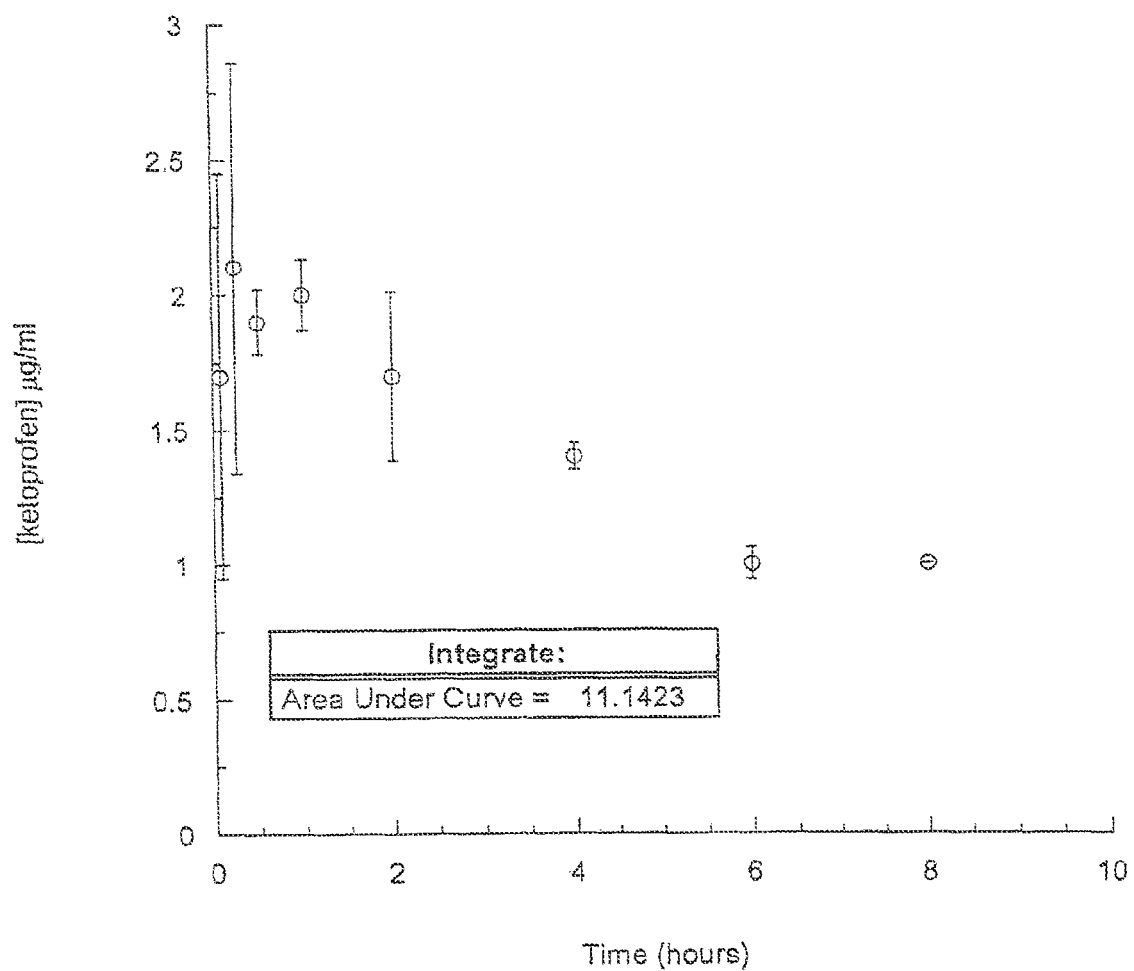
Figure 11:
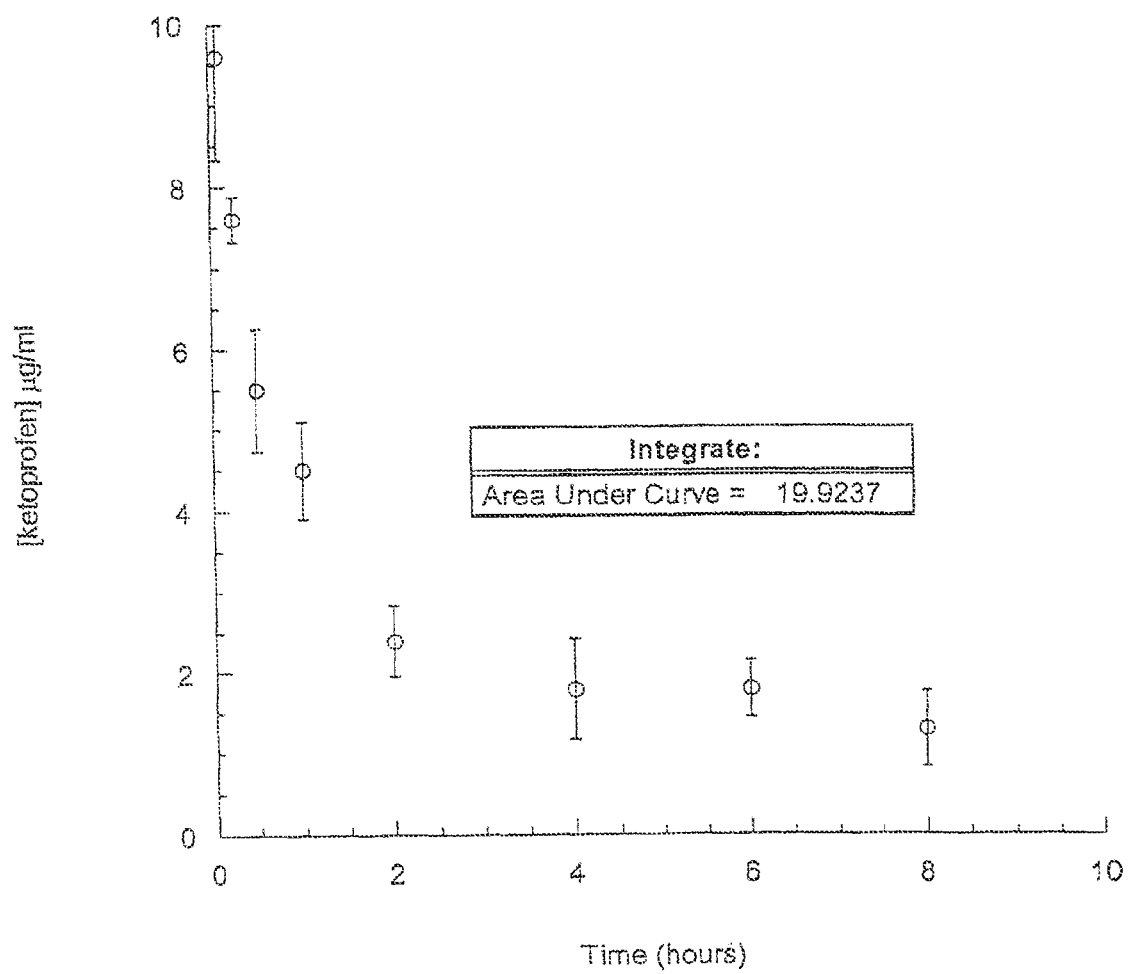
Figure 12:
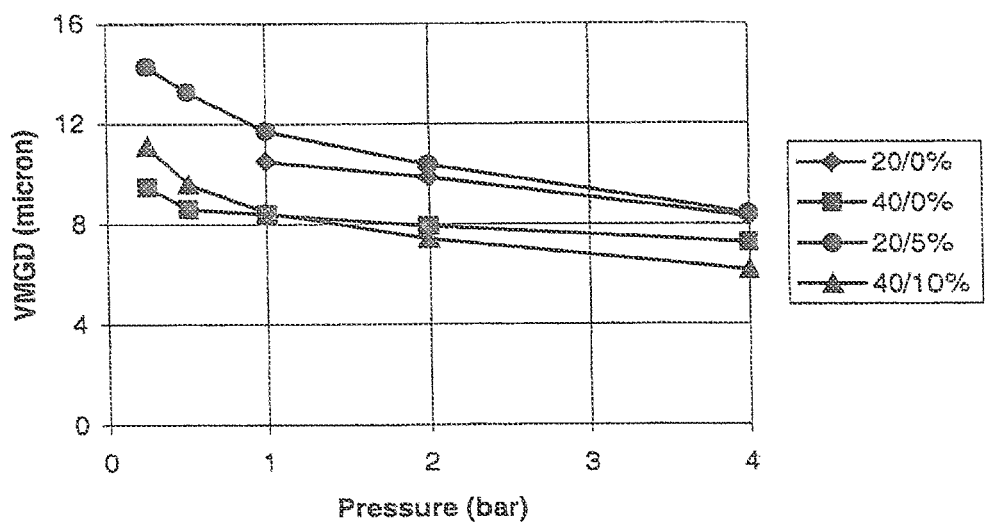
Figure 13A:
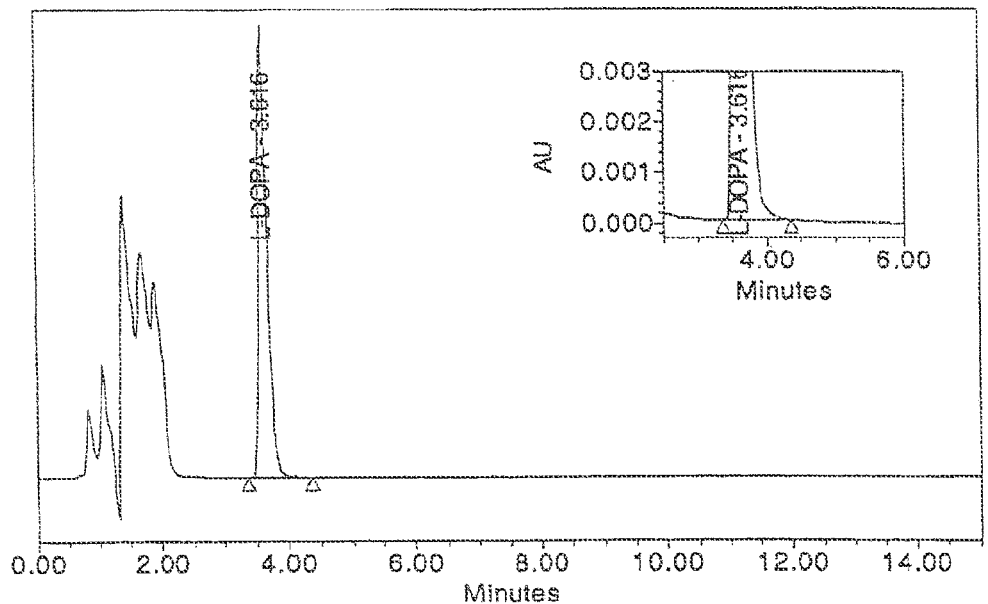
Figure 13B:
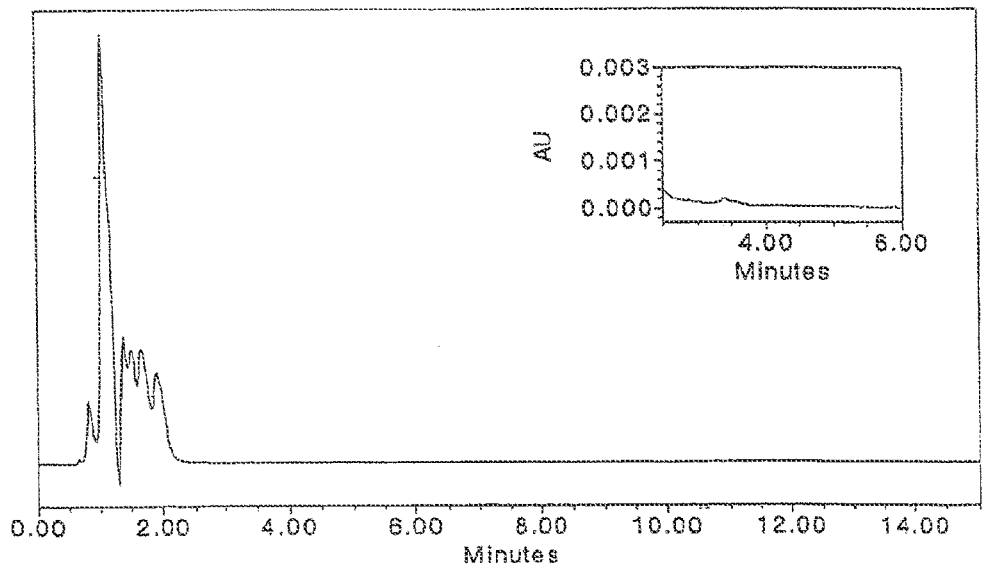
Figure 14A:
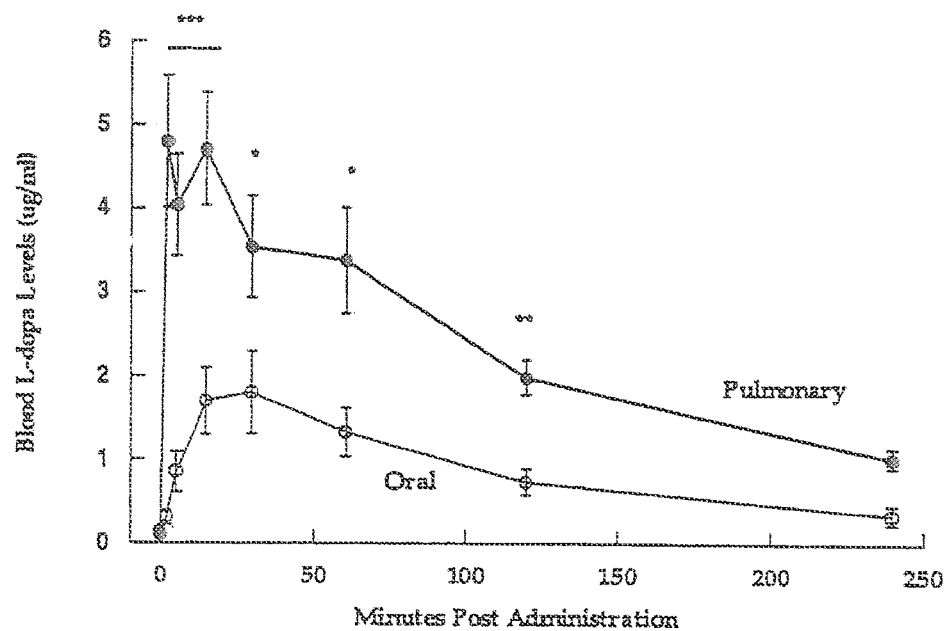
Figure 14B:
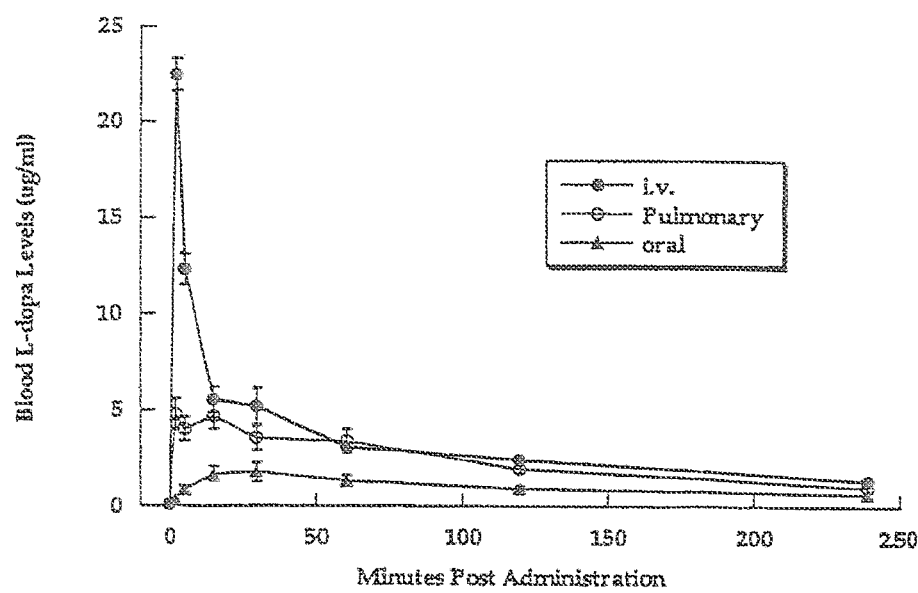

The results are provided in Table 7. The averages were calculated along with the standard errors and p values. The results are also presented graphically in FIG. 9-11, wherein FIG. 9 shows both data sets, FIG. 10 gives the oral dosing results and FIG. 11 shows the insufflation results. For FIG. 9, points with $p<0.05$ are marked with "*" and points with $p<0.01$ are marked with "". For FIGS. 10 and 11**, AUC (area under the curve) was performed via numerical integration of the curve with smooth interpolation.

At t=0, all rats showed ketoprofen levels below the detection limit for the assay. From t=5 min to t=60 min, the insufflated rats had significantly higher plasma levels of ketoprofen. At t=120 min and t=240 min, the plasma levels of ketoprofen of the two groups were statistically equivalent. At t=360 min and t=480, the plasma levels of ketoprofen for both groups approached the detection limit for the assay.

The ratio of the AUCs for insufflated rats vs. orally dosed was about 2. Since the plasma concentrations for ketoprofen at the early time points were statistically significant as well.

For the insufflated rats clearly occurred <15 min and for the orally dosed rats occurred between 15-60 min. Due to the large standard error and the relatively low plasma levels for this group, it is not possible to accurately determine the time required.

Pulmonary administration resulted in occurring very quickly (<15 min) compared to oral dosing (t=15 to 60 min).

The insufflated rats showed higher bioavailability compared to the orally dosed rats. This is unexpected as previous studies have shown ketoprofen to have consistently high (>90%) bioavailability in humans when dosed orally, subcutaneously or rectally. Since the pharmokinetic behavior of ketoprofen delivered orally is well-known, the anomalous results seen here for the orally dosed group do not invalidate the results seen for the insufflation group.

TABLE 7

| Time Min. | Oral Dosing Avg. (ug/ml) | Group St. Dev. | Pulmonary Avg. (ug/ml) | Dosing Group Std. Dev. | P Value |
|---|---|---|---|---|---|
| 0 | 1.0 | N/A | 1.0 | N/A | |
| 5 | 1.7 | 0.75 | 9.6 | 1.27 | 0.0003 |
| 15 | 2.1 | 0.76 | 7.6 | 0.28 | 0.0000 |
| 30 | 1.9 | 0.12 | 5.5 | 0.76 | 0.0012 |
| 60 | 2.0 | 0.13 | 4.5 | 0.60 | 0.0002 |
| 120 | 1.7 | 0.31 | 2.4 | 0.44 | 0.0929 |
| 240 | 1.4 | 0.05 | 1.8 | 0.63 | 0.2554 |
| 360 | 1.0 | 0.06 | 1.8 | 0.35 | 0.0224 |
| 480 | 1.0 | 0.00 | 1.3 | 0.47 | 0.2174 |

Average plasma levels of Ketoprofen from oral and pulmonary group

Example 7

The following experimental methods and instrumentation were employed to determine the physical characteristics of particles including L-DOPA and suitable for pulmonary delivery.

Aerodynamic diameter was analyzed using the API AeroDisperser and Aerosizer (TSI, Inc., St. Paul, Minn.) following standard procedures (Alkermes SOP #MS-034-005). Sample powder was introduced and dispersed in the AeroDisperser and then accelerated through a nozzle in the Aerosizer. A direct time-of-flight measurement was made for each particle in the Aerosizer, which was dependent on the particle's inertia. The time-of-flight distribution was then translated into a mass-based aerodynamic particle size distribution using a force balance based on Stokes law.

Geometric diameter was determined using a laser diffraction technique (Alkermes SOP #MS-021-005). The equipment consists of a HELOS diffractometer and a RODOS disperser (Sympatec, Inc., Princeton, N.J.). The RODOS disperser applies a shear force to a sample of particles, controlled by the regulator pressure of the incoming compressed air. The dispersed particles travel through a laser beam where the resulting diffracted light pattern produced is collected by a series of detectors. The ensemble diffraction pattern is then translated into a volume-based particle size distribution using the Fraunhofer diffraction model, on the basis that smaller particles diffract light at larger angles.

The aerodynamic properties of the powders dispersed from the inhaler device were assessed with a 2-stage MkII Anderson Cascade Impactor (Anderson Instruments, Inc., Smyrna, Ga.). The instrument consists of two stages that separate aerosol particles based on aerodynamic diameter. At each stage, the aerosol stream passes through a set of nozzles and impinges on the corresponding impaction plate. Particles having small enough inertia will continue with the aerosol stream to the next stage, while the remaining particles will impact upon the plate. At each successive stage, the aerosol passes through nozzles at a higher velocity and aerodynamically smaller particles are collected on the plate. After the aerosol passes through the final stage, a filter collects the smallest particles that remain.

Prior to determining the loading of drug within an AIR powder, the drug had to first be separated from the excipients within the powder. An extraction technique to separate L-Dopa from the excipient DPPC was developed. Particles were first dissolved in 50% chloroform/50% methanol. The insoluble L-Dopa was pelleted out and washed with the same solvent system and then solubilized in 0.5 M hydrochloric acid. DPPC was spiked with L-DOPA to determine recovery. Samples were injected onto a reverse phase high pressure liquid chromatography (HPLC) for analysis.

Separation was achieved using a Waters Symmetry C18 5-nm column (150-mm×4.6-mm ID). The column was kept at 30° C. and samples were kept at 25° C. Injection volume was 10 μL. The mobile phase was prepared from 2.5% methanol and 97.5% aqueous solution (10.5 g/L citric acid, 20 mg/L EDTA, 20 mg/L 1-octanesulfonic acid sodium salt monohydrate). Mobile phase was continually stirred on a stir plate and degassed through a Waters in-line degassing system. L-Dopa was eluted under isocratic conditions. Detection was performed using an ultraviolet detector set at wavelength 254 nm.

Since the average single oral dose of L-Dopa generally ranges from 100-150 mg, experiments were conducted to prepare particles suitable for inhalation which included high loads of L-Dopa. Formulations of 20% and 40% L-Dopa load were studied. Carbidopa, a decarboxylase inhibitor given in conjunction with L-Dopa to prevent peripheral decarboxylation, was also included at a 4:1 weight/weight (w/w) ratio in some of the formulations. L-Dopa and combination of L-Dopa and carbidopa were successfully sprayed with DPPC formulations. The optimal formulation consisted of L-Dopa and/or carbidopa, 20% (w/w) sodium citrate, and 10% (w/w) calcium chloride, and the remainder dipalmitoyl phosphatidyl choline (DPPC).

Details on formulations and the physical properties of the particles obtained are summarized in Table 8. The aerodynamic size or the mass median aerodynamic diameter (MMAD) was measured with an Aerosizer, and the geometric size or the volume median geometric diameter (VMGD) was determined by laser diffraction, and the fine particle fraction (FPF) was measured using a 2-stage Andersen Cascade Impactor. As shown in FIG. 12 and by the VMGD ratios in Table 8, the powders were flow rate independent. Scanning electron micrography was employed to observe the particles.

TABLE 8

| Load (%) ID L-Dopa/ Carbidopa | Yield (%) | VMGD (μm) at 2 bar | VMGD ratio 0.5/4.0 bar | MMAD (μm) | FPF (%) 5.6/3.4 |
|---|---|---|---|---|---|
| 20/0 | >40 | 9.9 | NA | 2.7 | NA |
| 40/0 | >40 | 8.0 | 1.2 | 3.3 | 42/17 |
| 20/5 | 42 | 10 | 1.6 | 3.1 | 64/38 |
| 40/10 | >20 | 7.4 | 1.6 | 3.8 | 40/14 |

L-Dopa through-process integrity appeared to be preserved through the formulation and spray drying process. L-Dopa was extracted from L-Dopa powders and analyzed by reverse phase HPLC. No impurities were detected in the L-Dopa powders (FIG. 13A); the early peaks eluted around 1-2 minutes are due to solvent as can be seen from FIG. 13B which is a blank sample that did not contain L-Dopa. The purity of L-Dopa recovered from the particles was 99.8% and 99.9% respectively for the 20% and 40% loaded particles.

To determine the loading of L-Dopa within the powder, the L-Dopa was first separated from the excipients in the formulation and then analyzed by reverse phase HPLC. Results of the L-Dopa recovery from the powders and the final load calculations are given in Table 9. Both extraction recoveries and load determination were satisfactory. The determined drug loading was approximately 87% of the nominal load. As used herein, the term "nominal load" refers to the total mass of bioactive agent expected in the mass of particles targeted for administration and represents the maximum amount of bioactive agent available for administration. As used herein, the term "nominal dose" refers to the total mass of bioactive agent which is present in the mass of particles targeted for administration and represents the maximum amount of bioactive agent available for administration.

TABLE 9

| Powder Formulation | Extraction recovery % | Actual load (%) |
|---|---|---|
| 20/0 | 100 ± 4.5 | 17.3 ± 0.2 |
| 40/0 | 101 ± 2.8 | 35.0 ± 5.4 |

Example 8

Determinations of plasma levels of L-Dopa were made following, IV injection, oral gavage, or insufflation into the lungs. Carbidopa generally is administered to ensure that peripheral decarboxylase activity is completely shut down. In this example, animals received an intraperitoneal (IP) injection of the peripheral decarboxylase inhibitor carbidopa (200 mg/kg) 1 hour prior to administration of L-Dopa. Under ketamine anesthesia, the animals were divided into 3 groups. In the first group of animals, L-Dopa (2 mg) was suspended in saline containing 1% methylcellulose and 1% ascorbic acid and given via oral gavage. In the second group, an insufflation technique was used for pulmonary administration of AIR particles loaded with L-Dopa (20% loading density). A laryngoscope was used to visualize the rat's epiglottis and the blunt-tip insufflation device (PennCentury Insufflation powder delivery device) was inserted into the airway. A bolus of air (3 cc), from an attached syringe, was used to delivery the pre-loaded powder from the chamber of the device into the animal's lungs. A total of 10 mg of powder (2 mg L-Dopa) was delivered. In the third group, a previously-placed femoral cannula was used to delivery a bolus (2-3 second) of L-Dopa (2 mg). Blood samples (200 μL) were withdrawn from each animal using the femoral cannula at the following timepoints: 0 (immediately prior to L-Dopa administration), 2, 5, 15, 30, 60, 120, and 240 minutes following L-Dopa administration. All samples were processed for L-Dopa determinations using HPLC.

The results of a pharmacokinetic study using the procedure described are shown in FIGS. 14A and 14B. The results of a comparison of pulmonary delivery of L-Dopa with oral administration are depicted in FIG. 14A. Following insufflation, peak plasma levels of L-Dopa were seen at the earliest time point measured (2 minutes) and began to decrease within 15 minutes of administration while still remaining elevated, relative to oral administration, for up to 120 minutes. In contrast, oral administration of L-Dopa resulted in a more gradual increase in plasma L-Dopa levels, which peaked at 15-30 minutes following administration and then decreased gradually over the next 1-2 hours.

Intravenous, oral and pulmonary delivery also were compared. The results are shown in FIG. 14B. This panel depicts the same data presented in FIG. 14A with the addition of the IV administration group which allows direct comparisons of the plasma L-Dopa levels obtained following all three routes of administration (pulmonary, oral, and IV). Data are presented as the mean±SEM μg L-Dopa levels/mL blood. Plasma levels of L-Dopa rapidly increased following intravenous (IV) administration. The highest levels of L-Dopa were seen at 2 minutes and decreased rapidly thereafter.

Bioavailability was estimated by performing area under the curve (AUC) calculations. Over the entire time course of the study (0-240 min), the relative bioavailability (compared to IV) of pulmonary L-Dopa was approximately 75% as compared 33% for oral L-Dopa. The relative bioavailability of pulmonary L-Dopa at 15 min and 60 min post administration was 38% and 62%, respectively, while that of oral L-Dopa was 9% and 24%, respectively.

Example 9

Pharmacodynamics evaluation of rats receiving L-Dopa also was undertaken. Rats received unilateral injections of the neurotoxin 6-OHDA into the medial forebrain bundle. Rats were then screened to assure successful striatal dopamine depletion using a standard apomorphine-induced turning paradigm. Beginning two weeks after surgery, animals were tested weekly for three weeks for apomorphine-induced rotation behavior. For this test, animals received an IP injection of apomorphine (0.25 mg/kg for the first test and 0.1 mg/kg for the following two tests) and were placed into a cylindrical Plexiglass bucket. Each 360-degree rotation was counted for 30 minutes and only those animals exhibiting >200 rotations/30 minutes (12/30 lesioned rats) were used in behavioral testing.

The lesioned rats were challenged with several motor tasks post L-Dopa administration. The data from the studies (placing task, bracing task, akinesia) further emphasized the advantage of pulmonary delivery over oral delivery.

In one test, animals passing the apomorphine challenge were tested using a "placing task". Prior to each test day, animals received an IP injection of the peripheral decarboxylase inhibitor carbidopa (200 mg/kg) as described above. Animals then received oral L-Dopa (0, 20 or 30 mg/kg) or pulmonary L-Dopa (0, 0.5, 1.0 or 2.0 mg of L-Dopa) and were tested 15, 30 60 and 120 minutes later. Throughout testing with oral and pulmonary delivery of L-Dopa, each animal received every possible drug combination in a randomized fashion.

The pharmacodynamics "placing task" required the animals to make a directed forelimb movement in response to sensory stimuli. Rats were held so that their limbs were hanging unsupported. They were then raised to the side of a table so that their bodies were parallel to the edge of the table. Each rat received 10 consecutive trials with each forelimb and the total number of times the rat placed its forelimb on the top of the table was recorded.

Figure 15A:
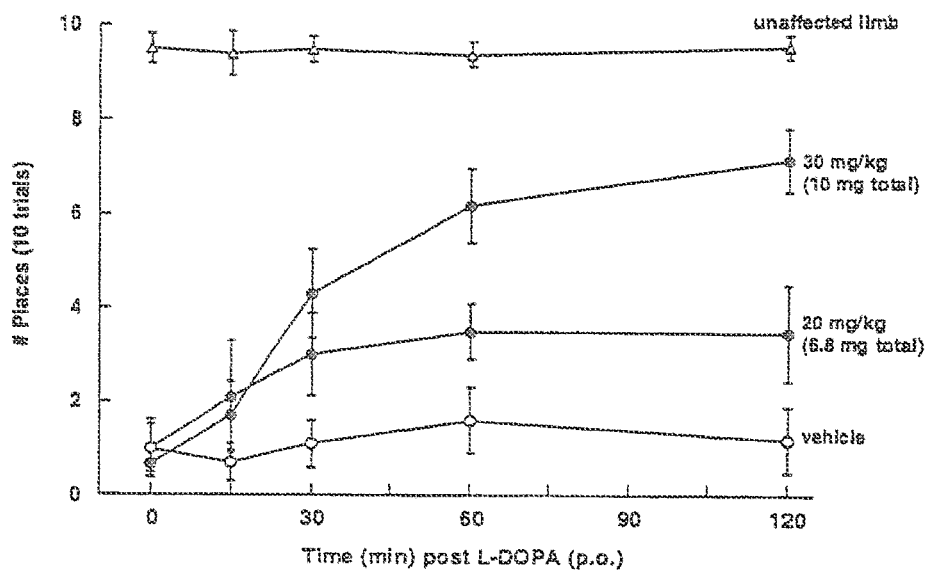
Figure 15B:
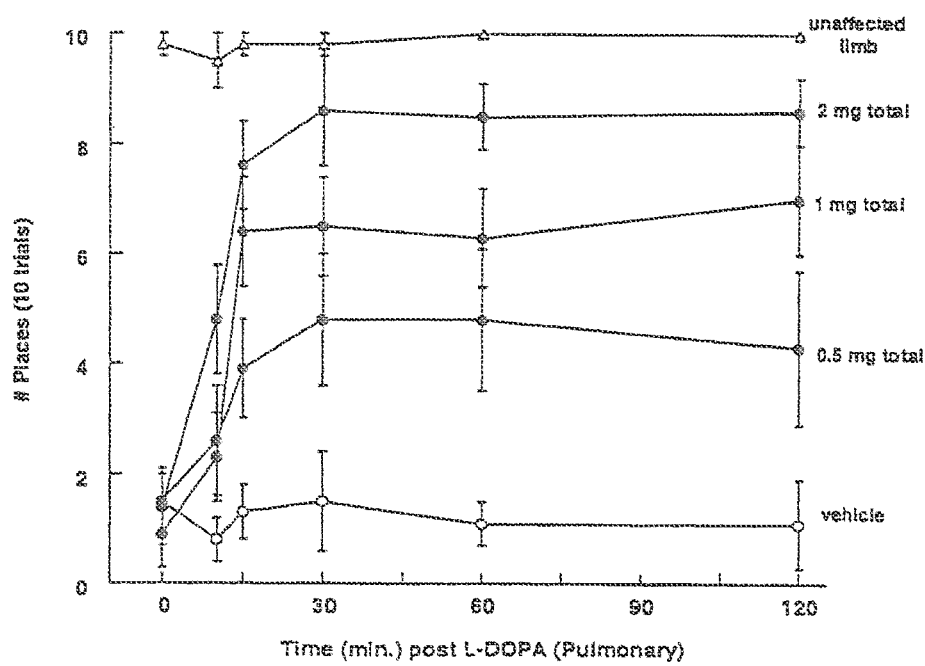

Results from a "placing task" tests are shown in FIGS. 15A and 15B. At baseline (t=0; immediately prior to L-Dopa administration), the animals performed nearly perfectly on this task with the unaffected limb, making greater than 9/10 correct responses. In contrast, the animals were markedly impaired in their ability to perform the same task with the impaired limb, making approximately 1 correct response over the 10 trials.

Oral L-Dopa (FIG. 15A) produced a dose-related improvement in performance with the impaired limb. At the highest dose tested (30 mg/kg), performance was improved, relative to saline control, within 30 minutes and peaked between 1-2 hours after drug administration. The lower dose (20 mg/kg) also improved performance slightly with maximal effects at 60 minutes and stable performance thereafter. No changes were noted following administration of the saline control.

In contrast to oral administration, performance on the "placing task" rapidly improved following pulmonary delivery of L-Dopa, as seen in FIG. 15B. At the highest dose tested, significant improvements occurred within 10 minutes, with peak benefits observed within 15-30 minutes (as opposed to 1-2 hours with oral administration). These effects were dose-related, with significant improvements seen with doses as low as 0.5 mg of L-Dopa. In comparison to the recovery shown with oral delivery, the behavioral improvements were seen with markedly lower total doses using the pulmonary route. For instance, the extent of recovery with 30 mg/kg of L-Dopa given orally was comparable to the recovery seen with 1 mg of L-Dopa given by the pulmonary route (note that 1 mg of pulmonary L-Dopa is equivalent to approximately 3 mg/kg, given that the animals body weight was approximately 300 g). Accordingly, when the L-Dopa doses were normalized by body weight, this represented nearly a 10-fold difference in the drug required to produce equivalent efficacy. Finally, the persistence of the behavioral improvements was comparable using the two delivery routes.

Figure 16A:
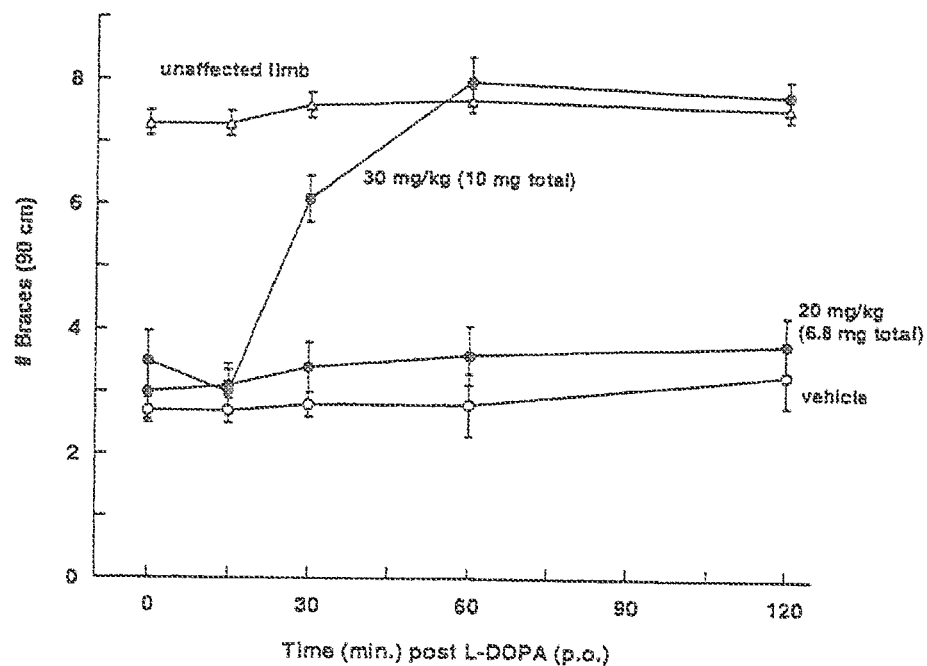
Figure 16B:
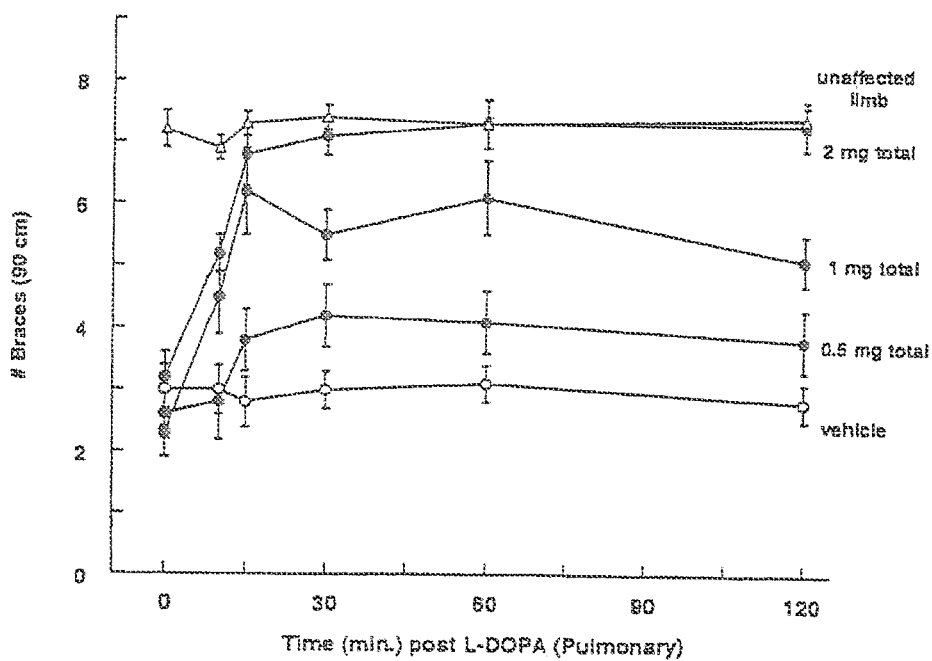

Results from a bracing test are shown in FIGS. 16A and 16B. This test was performed using the same animals and at the same time as the "placing task" test described above. Rats were placed on a smooth stainless steel surface and gently pushed laterally 90 cm at approximately 20 cm/second. The number of steps the rat took with the forelimb on the side in which the rat was moving was recorded. Each trial included moving the rat 2 times in each direction.

The animals demonstrated a profound impairment in their ability to perform this task with the impaired limb, making approximately 3 responses compared to approximately 7 with the unaffected limb, as seen in FIG. 16A. Again, oral administration improved performance on this task in a dose-related manner. Administration of 30 mg/kg (approximately 10 mg L-Dopa) improved performance within 30 minutes. Maximal effects were seen within 60 minutes and remained stable thereafter. A lower dose of oral L-Dopa (20 mg/kg or approximately 7 mg of L-Dopa) slightly improved performance. Again, administration of the saline control did not affect performance.

Figure 17A:
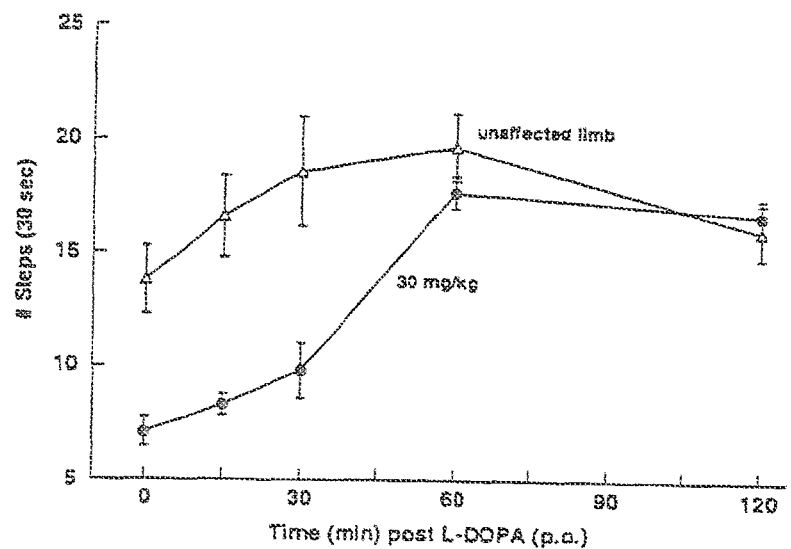
Figure 17B:
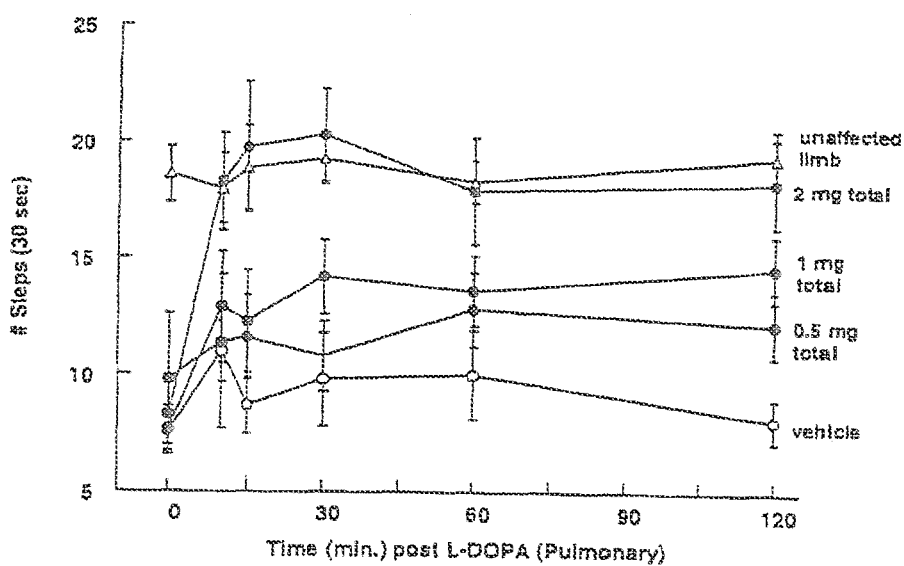

In contrast to oral administration, performance on this task rapidly improved following pulmonary administration of L-Dopa, as shown in FIG. 16B. Significant improvements were seen within 10 minutes, with peak benefits observed within 15-30 minutes (as opposed to 30-60 minutes with oral administration). These effects were dose-related, with modest, but statistically significant improvements seen with as low as 0.5 mg (equivalent to approximately 1.5 mg/kg). As with the other functional tests, the behavioral improvement achieved following pulmonary L-Dopa occurs at doses far below those required to achieve a similar magnitude of effect following oral delivery. Finally, the persistence of the behavioral improvements was comparable using the two delivery routes. A functional akinesia pharmacodynamics study also was conducted. The results are shown in FIGS. 17A and 17B. This test was performed using the same animals and at the same time as the two preceding tests. In this task, the animal was held so that it was standing on one forelimb and allowed to move on its own. The number of steps taken with the forelimb the rat was standing on was recorded during a 30 second trial for each forelimb.

As was seen with the placing and bracing tests, the animals demonstrated a profound impairment in their ability to perform the akinesia task with the impaired limb. While the animals made approximately 17 steps with the normal limb, they made fewer than half this number with the impaired limb (range=0-10 steps). Oral administration (FIG. 17A) improved performance on this task in a dose-related manner. Administration of 30 mg/kg (approximately 10 mg L-Dopa) improved performance within 30 minutes and maximal effects were seen within 60 minutes. A lower dose of oral L-Dopa (20 mg/kg or approximately 6.8 mg of L-Dopa) produced the same pattern of recovery although the absolute magnitude of improvement was slightly lower than that seen with the higher dose of L-Dopa. Performance remained stable between 60 and 120 minutes following administration of both doses. Administration of the saline control did not affect performance.

In contrast to oral administration, performance on this task rapidly improved following pulmonary administration of L-Dopa, as depicted in FIG. 17B. Significant improvements were seen within 10 minutes, with peak benefits observed within 15-30 minutes (as opposed to 60 minutes with oral administration). These effects were dose-related statistically significant ($p<0.05$) improvements seen with as low as 1.0 mg. As with the other functional tests, the behavioral improvement achieved following pulmonary L-Dopa occurred at doses far below those required to achieve a similar magnitude of effect following oral delivery. Finally, the persistence of the behavioral improvements was comparable using the two delivery routes.

Animals also were tested on a standard pharmacodynamics rotation test known to be a sensitive and reliable measure of dopamine activity in the brain. For this test, animals received either oral L-Dopa (30 mg/kg or approximately 10 mg total) or pulmonary L-Dopa (2 mg total). These doses were chosen for this test because they represent the doses of L-Dopa shown to produce maximal efficacy in the previous functional tests. Following dosing, animals were placed into a cylindrical Plexiglas bucket. Each 360-degree rotation was counted and grouped into 5 minute bins over a 120 minute test period. Animals were also tested for rotation behavior with and without pre-treatment with cabidopa.

All of the animals used in these studies received unilateral injections of 6-OHDA, a neurotoxin specific for dopamine neurons in the brain. Because the dopamine depletions are unilateral, the uninjected side remained intact and still able respond to changes in dopamine activity. When these animals were injected with a dopamine agonist (i.e. L-Dopa) brain dopamine activity was stimulated preferentially on the intact side. This resulted in an asymmetrical stimulation of motor activity that was manifested as a turning or rotational behavior. The onset and number of rotations provided a measure of both the time course as well as the extent of increased dopamine activity.

Figure 18:
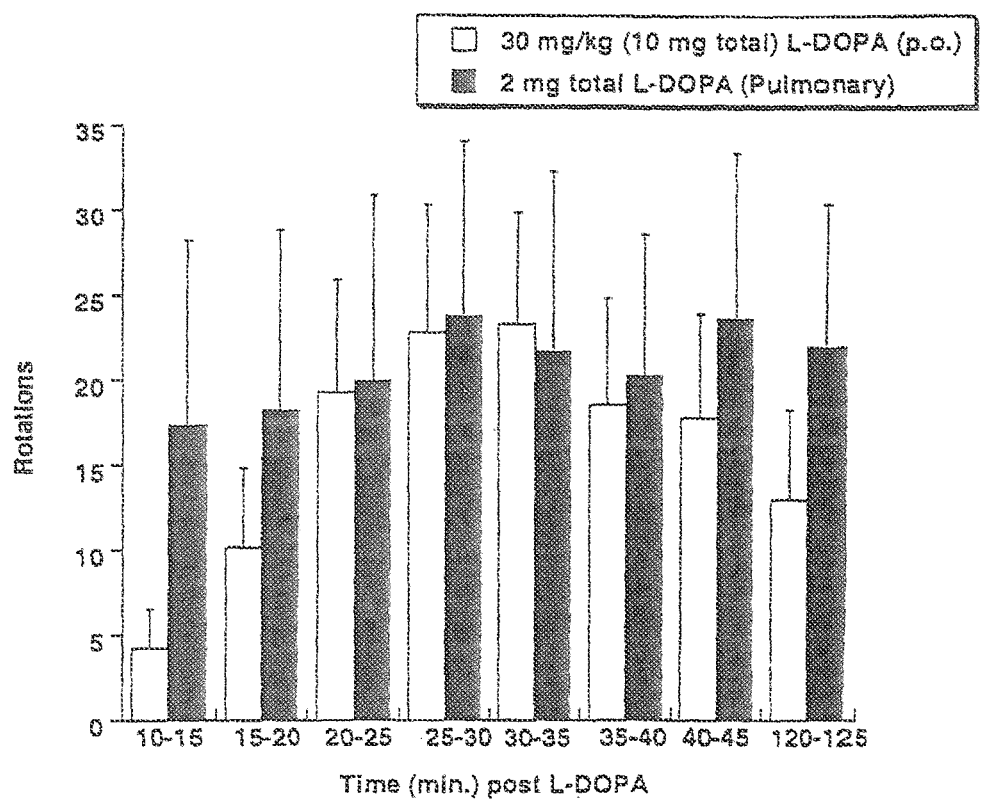

The results are shown in FIG. 18. Oral administration of L-Dopa produced a marked clockwise rotation behavior that was modest during the first 10-15 minutes post L-Dopa administration (<5 rotations/animal). During the next 20 minutes, the number of rotations increased markedly, with peak levels occurring approximately 30 minutes after L-Dopa indicating increased dopamine activity in the intact striatum of the brain. During the next 90 minutes, the number of rotations gradually decreased, but this decrease, relative to peak levels, did not reach statistical significance ($p>0.05$).

In contrast to oral administration, pulmonary delivery of L-Dopa rapidly increased rotation behavior indicating much more rapid conversion of L-Dopa to dopamine in the intact striatum. Rotations in this group were greater than 3 times that produced by oral delivery within the first 10-15 minutes. The numbers of rotations increased slightly, peaked at 25-30 minutes, and remained relatively stable thereafter. While a trend towards increased rotations, relative to oral delivery, was see 120 minutes after dosing, this did not reach statistical significance ($p>0.05$). Rotation behavior was virtually eliminated in animals that did not receive pre-treatment with carbidopa (data not shown).

Example 10

The purpose of the following experiment is to test the relative bioavailability of various compositions comprising at least a carrier particle and optionally an agent. Unless otherwise indicated, where spray-dried particles were used, they were prepared following the steps in the Examples above. Characteristics of the particles prepared fall within the ranges previously disclosed. The formulations are set out in Table 10 below.

Tests were conducted using various formulations of salmeterol. Unless otherwise indicated, micronized salmeterol xinafoate was used in the preparation of the particles. Two such formulations are Formulation 1 (F1) and Formulation 2 (F2) in Table 10. F1 was comprised of 69% DPPC/20% Sodium citrate/10% Calcium chloride/1% salmeterol. F2 was comprised of 29.5% DPPC/29.5% DPPE/20% lactose/20% sodium citrate/1% salmeterol. For comparison, formulations of F1 and F2 both without salameterol were prepared. Two salmeterol containing controls SX1 and SX2 were used in the experiments testing F1 and F2 respectively.

TABLE 10

| in wgt. % | Salmeterol | DPPC | DPPE | Sodium Citrate | Calcium Chloride | Lactose |
|---|---|---|---|---|---|---|
| F-1 | 1 | 69 | — | 20 | 10 | — |
| F-1 without salmeterol | 0 | 70 | — | 20 | 10 | — |
| F-2 | 1 | 29.5 | 29.5 | 20 | — | 20 |
| F-2 without salmeterol | 0 | 30 | 30 | 20 | — | 20 | prepare the pre-spray drying solution of F1, 200 mg of sodium citrate and 100 mg of calcium chloride were dissolved in 300 ml of water. 690 mg of DPPC and 10 mg salmeterol was dissolved in 700 ml EtOH. The two solutions were combined to form a 1 liter solution, 70% EtOH/30% water, 1 g/liter of solids.

To prepare the pre-spray drying solution of F2, 200 mg of sodium citrate and 200 mg of lactose were dissolved in 300 ml of water. 295 mg of DPPC, 295 mg of DPPE and 10 mg salmeterol was dissolved in 700 ml EtOH. The two solutions were combined to form a 1 liter solution, 70% EtOH/30% water, 1 g/liter of solids.

The pre-spray dried solutions were spray dried as described above producing dry particle used in the experiments below.

Example 11

The dry particle formulations (AIR particles) produced above were prepared for administration. The AIR particles, in this case F1 and F2 spray dried without salmeterol, were placed in the capsule and weighed. Thereafter desired active compounds (F1, F2) were placed on top of the AIR particles and the weight was recorded. Specifically, the F-1 formulation was placed with the F1 without salmeterol formulation and the F-2 formulation was placed with the F-2 without salmeterol formulation. The final mass of the contents of the capsule totaled 1.0 mg. The capsule was closed and the contents mixed by turning the capsule over repeatedly. This process produced a "blend" in the capsule which was administered in these experiments.

For SEREVENT® test formulations, SEREVENT® 1 and SEREVENT® 2 as the active compound were prepared. SEREVENT® is a registered trademark of GlaxoWellcome, Research Triangle, N.C. It is a formulation of salmeterol xinafoate as the racemic form of the 1-hydroxy-2-naphthoic acid salt of salmeterol. The active component of the formulation is salmeterol base, a highly selective beta$_2$-adrenergic bronchodilator. The chemical name of salmeterol xinafoate is 4-hydroxy-$\alpha^1$-[[[6-(4-phenylbutoxy)hexyl]amino]methyl]-1,3-benezenedimethanol, 1-hydroxy-2-naphthalenecarboxylate.

The procedure for filling the capsule above was generally followed. However in the test formulations using SEREVENT® 1 and SEREVENT® 2, AIR particles were not used. Instead micronized lactose powder was placed first in the capsule and the weight was recorded. Thereafter, SEREVENT® was placed on the lactose powder. As above, the final mass of the contents of the capsule totaled 1.0 mg. The capsule was closed and the contents mixed by turning the capsule over repeatedly. This process produced a "blend" in the capsule. Finally, two salmeterol containing controls, SX1 and SX2 were used in the experiments, in which SEREVENT® was blended with AIR particles without salmeterol (carriers). AIR particles, in this case F-1 without salmeterol particles, were placed first in the capsule and the weight was recorded. Thereafter, SEREVENT® was placed on the AIR particles. As above, the total mass of the contents of the capsule was 1.0 mg. The capsule was closed and the contents mixed by turning the capsule over repeatedly. This process produced a "blend" in the capsule which was administered in these experiments.

Example 12

A whole body plethysmography method for evaluating pulmonary function in guinea pigs has been used. Anesthetized animals were administered test formulations by intratracheal insufflation. This system allowed individual guinea pigs to be challenged repeatedly over-time with methacholine given by nebulization. A calculated measurement of airway resistance based on flow parameters, PenH (enhanced pause), was specifically used as a marker of protection from methacholine-induced bronchoconstriction.

Specifically, the system used was the BUXCO whole-body unrestrained plethysmograph system with BUXCO XA pulmonary function software (BUXCO Electronics, Inc., Sharon, Conn.). This protocol is described in Silbaugh and Mauderly ("Noninvasive Detection of Airway Constriction in Awake Guinea Pigs," *American Physiological Society*, 84:1666-1669 (1984) and Chong et al., "Measurements of Bronchoconstriction Using Whole-Body Plethysmograph: Comparison of Freely Moving Versus Restrained Guinea Pigs," *Journal of Pharmacological and Toxicological Methods*, 39(3):163-168 (1998)). Baseline pulmonary function (airway hyperresponsiveness) values were measured prior to any experimental treatment. Airway hyperresponsiveness was then assessed in response to saline and methacholine at various timepoints (2-3, 16, 24 and 42 h) following administration of salmeterol formulations. Average PenH was calculated from data collected between 4 and 9 minutes following challenge with saline or methacholine. The percent of baseline PenH at each timepoint was calculated for each experimental animal. Values from animals that received the same formulation were subsequently averaged to determine the mean group response (±standard error) at each timepoint.

Male Hartley guinea pigs were obtained from Elm Hill Breeding Labs (Chelmsford, Mass.). The powder amount (1 milligram in a capsule) was transferred into the insufflator sample chamber insufflation device for guinea pigs, Penn Century (Philadelphia, Pa.). The delivery tube of the insufflator was inserted through the mouth into the trachea and advanced until the tip of the tube was about a centimeter from the carina (first bifurcation). The volume of air used to deliver the powder from the insufflator sample chamber was 3 mL, delivered from a 10 mL syringe. In order to maximize powder delivery to the guinea pig, the syringe was recharged and discharged two more times for a total of three air discharges per powder dose. Methacholine challenges were performed at time points 2-3, 16 and 24 h after powder administration.

The tests were repeated using the formulation ingredients and amounts are set out on Table 11 below.

TABLE 11

| | % Salmeterol | Mass of salmeterol in spray-dried in AIR particle (μg) | Mass of salmeterol in Serevent (μg) | Total mass of AIR particles containing salmeterol (μg) | Total mass of Serevant powder containing salmeterol (μg) | AIR particles without salmeterol (carrier) (μg) | Micronized Lactose Powder (μg) | Total |
|---|---|---|---|---|---|---|---|---|
| F-1 (0.5) | 1 | 0.5 | | 50 | | 950 | | 1 mg |
| F-1 (1.0) | 1 | 1 | | 100 | | 900 | | 1 mg |
| F-1 (2.0) | 1 | 2 | | 200 | | 800 | | 1 mg |
| F-1 no salmet. | 0 | 0 | | 0 | | 1000 g or 1 mg | | 1 mg |
| F-2 (0.5) | 1 | 0.5 | | 50 | | 950 | | 1 mg |
| F-2 (1.0) | 1 | 1 | | 100 | | 900 | | 1 mg |
| F-2 (2.0) | 1 | 2 | | 200 | | 800 | | 1 mg |
| F-2 no salmet. | 0 | 0 | | 0 | | 1000 g or 1 mg | | 1 mg |
| SX1 (0.5) | 0.4 | | 0.5 | | 125 | 875 | | 1 mg |
| SX2 (1.0) | 0.4 | | 1 | | 250 | 750 | | 1 mg |
| Serevent ® 1 | 0.4 | | 0.5 | | 125 | | 875 | 1 mg |
| Serevent ® 2 | 0.4 | | 1 | | 250 | | 750 | 1 mg |

Example 13

Figure 19:
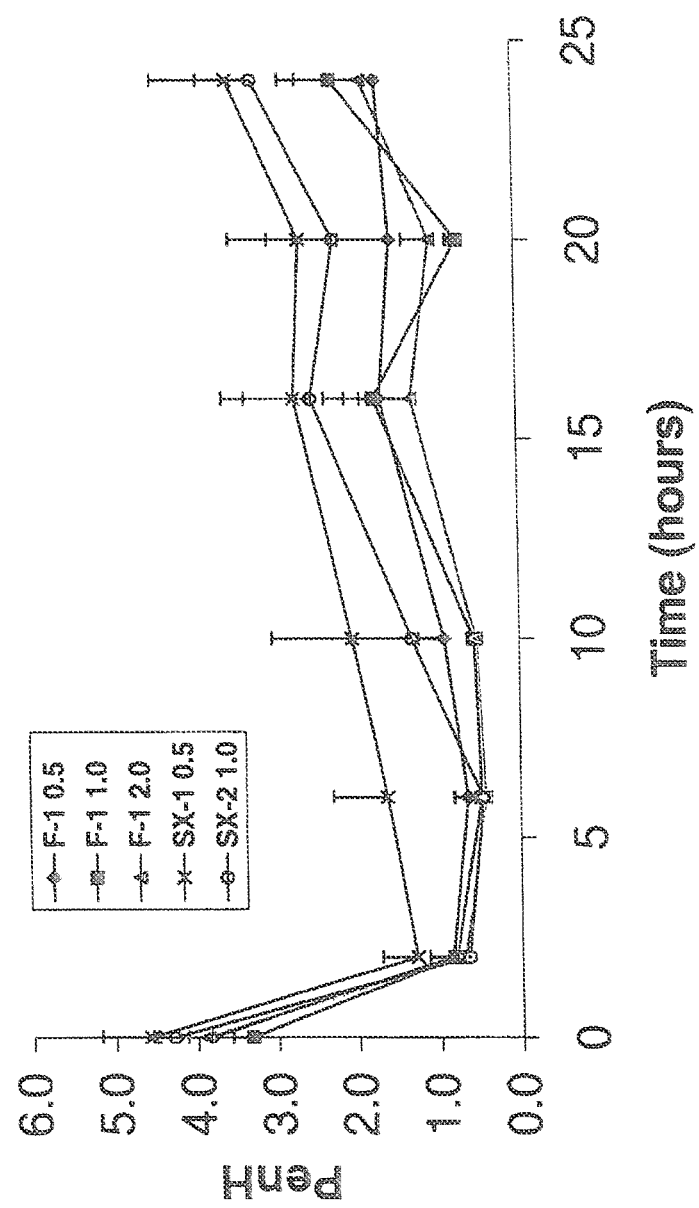

In one experiment, the procedures in Example 12 were followed. The formulations F-1 (0.5), F-1 (1.0), F-1 (2.0), SX-1 (0.5) and SX-2 (1.0) which are described in Table 11, were administered to the animals. The F-1 series of formulations contain salmeterol, DPPC, sodium citrate and calcium chloride. Using flow parameters, PenH (enhanced pause or the measurement of airway resistance) was calculated and recorded for each animal. The animals were observed and tested for 25 hours. The results are shown in FIG. 19. SX formulations contain SEREVENT™, a commercially available form of salmeterol. Salmeterol-containing AIR particles (F-1 series in Tables 10 and 11) compare favorably to the Serevent-containing formulations (SX1 (0.5) and SX2 (1.0) in Table 11 when blended with AIR particles without salmeterol (sometimes referred to as blanks or placebo particles). The F-1 formulations generally showed less airway resistance than the SX formulations. Further, all the F-1 formulations consistently showed less airway resistance than SX-1 (0.5). Beginning at about 10 hours after administration, all F-1 formulations showed significant and sustained low airway resistance when compared to either SX-1 or SX-2.

Example 14

Figure 20:
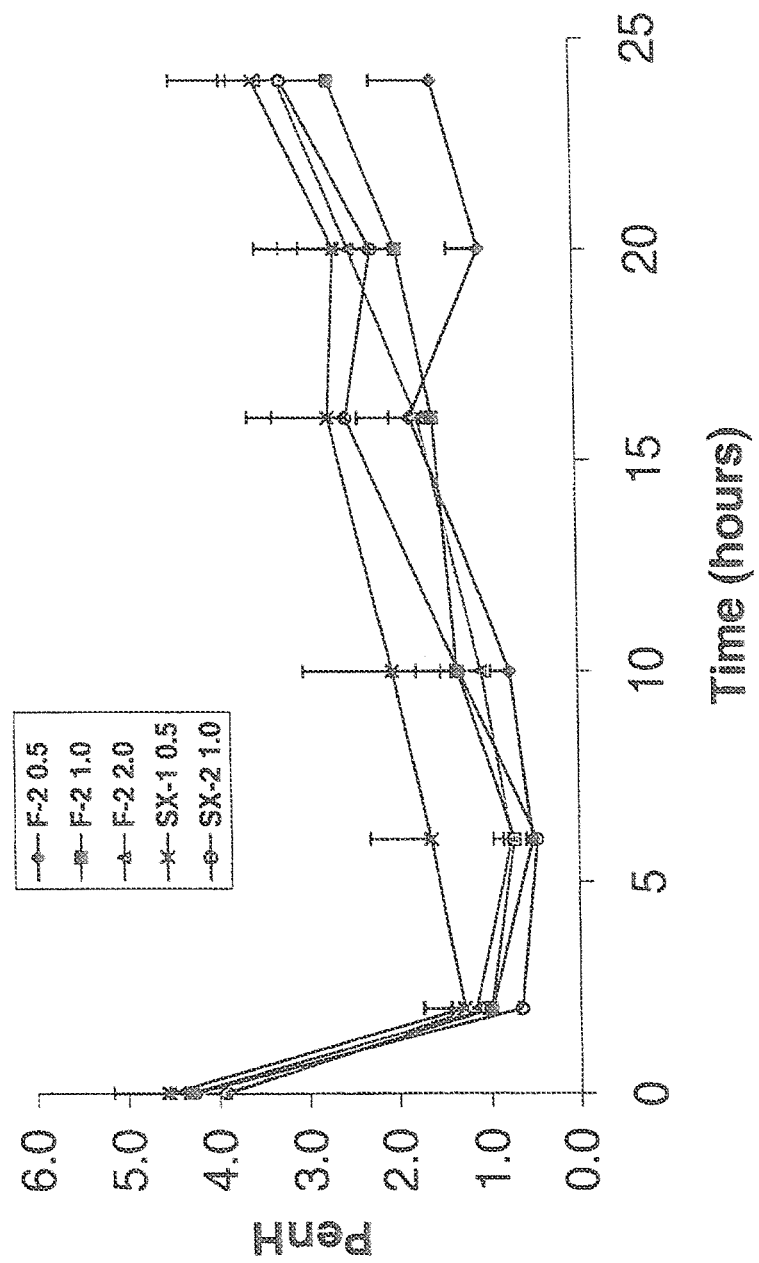

In another experiment, following the procedures in Example 12, the formulations F-2 (0.5), F-2 (1.0), F-2 (2.0), SX-1 (0.5) and SX-2 (1.0) which are described in Table 11 were administered to the animals. The F-2 series of formulations contain salmeterol, DPPC, DPPE, sodium citrate and lactose. Using flow parameters, PenH (enhanced pause or the measurement of airway resistance) was calculated and recorded for each animal. The animals were observed and tested for 25 hours. The results are shown in FIG. 20. SX formulations contain Serevent, the commercially available form of salmeterol. Salmeterol-containing AIR particles (F-2 series on Tables 10 and 11) compare favorably to the Serevent-containing formulations (SX1 (0.5) and SX2 (1.0) in Table 11) when blended with AIR particles without salmeterol (sometimes referred to as blanks or placebo particles). The F-2 formulations generally showed less airway resistance than the SX formulations. Also, all the F-2 formulations consistently showed less airway resistance than SX-1 (0.5).

Example 15

In another experiment, the above procedures were followed. The formulations F-1 (0.5), F-1 (1.0), F-1 (2.0), Serevent 1 (0.5) and Serevent (1.0) which are described in Table 11, were administered to the animals. The results comparing the Serevent formulations to the F-1 series (data not shown) were consistent with the results when comparing SX formulations to the F-1 series. Importantly, the results indicate that the AIR particles (blanks or placebo) when used as carriers perform equally well if not better than lactose. Lactose is an FDA approved, commercially available carrier. However, lactose cannot get to the deep lung. As shown in Example 3, AIR particles do reach the deep lung and are capable of escorting or accompanying the desired agent, such as salmeterol in this experiment, to the site of deposition of the agent.

Example 16

In another experiment, the above procedures were followed. The formulations F-2 (0.5), F-2 (1.0), F-2 (2.0), Serevent 1 (0.5) and Serevent (1.0) which are described in Table 11, were administered to the animals. Once again, the results observed in the comparison of the Serevent formulations to the F-2 series (data not shown) were the consistent with the results when comparing SX formulations to the F-2 series. These results support the conclusions described in Example 15 above.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of delivering an agent to the pulmonary system, in a single, breath-activated step, using a dry powder inhaler, comprising administering particles comprising an agent from a receptacle having a mass consisting of said particles to a subject's respiratory tract, wherein:
   i) about 50% or more of the mass of dry powder particles stored in the receptacle is delivered to the lungs of the subject; and
   ii) about 5 milligrams or more of the agent is delivered to the lungs of the subject.

2. The method of claim 1, wherein the particles have a tap density of about 0.4 g/cm$^3$ or less.

3. The method of claim 1, wherein the particles have a tap density of about 0.1 g/cm$^3$ or less.

4. The method of claim 2, wherein delivery is primarily to the deep lung.

5. The method of claim 2, wherein the particles are spray-dried particles.

6. The method of claim 1, wherein the agent is non-crystalline.

7. The method of claim 1, wherein at least 50% of the particles have a fine particle fraction less than 4.0 µm.

8. The method of claim 1, wherein at least 75% of the particles have a fine particle fraction less than 6.8 µm.

* * * * *